US006738502B1

(12) United States Patent
Coleman et al.

(10) Patent No.: US 6,738,502 B1
(45) Date of Patent: May 18, 2004

(54) MULTISPECTRAL TAXONOMIC IDENTIFICATION

(75) Inventors: William Coleman, Mountain View, CA (US); Michael A. Tanner, Hayward, CA (US); Christopher M. Silva, Sunnyvale, CA (US); Edward Bylina, San Jose, CA (US); Steven J. Robles, San Jose, CA (US); Michael R. Dilworth, Santa Cruz, CA (US); Douglas C. Youvan, San Jose, CA (US); Mary M. Yang, San Jose, CA (US)

(73) Assignee: Kairos Scientific, Inc., San Diego, CA (US)

( * ) Notice: Subject to any disclaimer, the term of this patent is extended or adjusted under 35 U.S.C. 154(b) by 575 days.

(21) Appl. No.: 09/585,951

(22) Filed: Jun. 2, 2000

Related U.S. Application Data

(60) Provisional application No. 60/137,458, filed on Jun. 4, 1999.

(51) Int. Cl.[7] .............................. G06K 9/00; G06K 9/46; G06K 9/36
(52) U.S. Cl. ....................... 382/133; 382/167; 382/191; 382/287
(58) Field of Search .................................. 382/133, 134, 382/129, 167, 151, 287, 309, 191; 336/39, 51; 702/19, 85; 345/601; 358/535, 504

(56) References Cited

U.S. PATENT DOCUMENTS

| | | | |
|---|---|---|---|
| 3,827,804 A | * | 8/1974 | Miller et al. .................. 356/39 |
| 4,794,460 A | * | 12/1988 | Shiota ......................... 386/128 |
| 4,851,330 A | | 7/1989 | Kohne et al. |
| 5,303,165 A | * | 4/1994 | Ganz et al. ................... 356/319 |
| 5,548,661 A | * | 8/1996 | Price et al. .................. 382/133 |
| 5,668,596 A | * | 9/1997 | Vogel ....................... 348/222.1 |
| 5,856,871 A | | 1/1999 | Cabib et al. |
| 5,869,237 A | | 2/1999 | Ward et al. |
| 5,871,932 A | | 2/1999 | Bar-Am et al. |
| 5,906,919 A | | 5/1999 | Garini et al. |
| 5,912,165 A | | 6/1999 | Cabib et al. |
| 5,936,731 A | | 8/1999 | Cabib et al. |
| 5,991,028 A | | 11/1999 | Cabib et al. |
| 6,007,994 A | | 12/1999 | Ward et al. |
| 6,007,996 A | | 12/1999 | McNamara et al. |
| 6,018,587 A | | 1/2000 | Cabib |
| 6,055,325 A | | 4/2000 | Garini et al. |
| 6,060,251 A | | 5/2000 | Ward et al. |
| 6,066,459 A | | 5/2000 | Garini et al. |
| 6,141,461 A | * | 10/2000 | Carlini ....................... 382/261 |
| 6,259,807 B1 | * | 7/2001 | Ravkin ....................... 382/133 |

FOREIGN PATENT DOCUMENTS

WO   PCT/US97/08237   5/1997

OTHER PUBLICATIONS

Tanner et al., Multispectal Bacterial Identification, SPIE vol. 3913, 2000, 45–53.*

* cited by examiner

*Primary Examiner*—Daniel Mariam
*Assistant Examiner*—Shefali Patel
(74) *Attorney, Agent, or Firm*—Fenwick & West LLP; Michael J. Shuster

(57) ABSTRACT

The present invention provides an instrument and methods for a multispectral optical technique that can simultaneously classify individual biological cells within mixed populations. This invention, known as Multispectral Taxonomic Identification (MTID), shows that microscopy can be combined with a software analysis program to measure and categorize the fluorescence and other spectroscopically identifiable signals from complex populations of cells in situ, without cultivation. The invention thus enables high-throughput screening of cells for taxonomic classification.

20 Claims, 23 Drawing Sheets

(11 of 23 Drawing Sheet(s) Filed in Color)

| | Channel 1 | Channel 2 | Channel 3 | Channel 4 | Channel 5 | Channel 6 | Channel 7 | Channel 8 |
|---|---|---|---|---|---|---|---|---|
| Dye 1 | 270 | 89 | 31 | 51 | 109 | 35 | 111 | 40 |
| Dye 2 | 155 | 398 | 31 | 46 | 119 | 38 | 125 | 41 |
| Dye 3 | 84 | 84 | 656 | 93 | 127 | 41 | 134 | 39 |
| Dye 4 | 84 | 83 | 52 | 959 | 219 | 63 | 139 | 58 |
| Dye 5 | 90 | 90 | 44 | 181 | 1129 | 451 | 165 | 27 |
| Dye 6 | 80 | 80 | 50 | 75 | 853 | 1910 | 208 | 89 |
| Dye 7 | 91 | 83 | 40 | 68 | 155 | 85 | 2563 | 300 |
| Dye 8 | 94 | 103 | 28 | 52 | 144 | 66 | 888 | 2903 |

| | Channel 1 | Channel 2 | Channel 3 | Channel 4 | Channel 5 | Channel 6 | Channel 7 | Channel 8 |
|---|---|---|---|---|---|---|---|---|
| Dye 1 | 12.287 | -2.340 | -0.371 | -0.328 | -0.820 | 0.050 | -0.302 | -0.087 |
| Dye 2 | -4.441 | 8.172 | -0.136 | -0.056 | -0.400 | 0.026 | -0.162 | -0.032 |
| Dye 3 | -0.789 | -0.592 | 4.369 | -0.290 | -0.290 | 0.017 | -0.126 | -0.018 |
| Dye 4 | -0.501 | -0.362 | -0.166 | 3.070 | -0.508 | 0.043 | -0.077 | -0.036 |
| Dye 5 | -0.457 | -0.347 | -0.079 | -0.496 | 3.212 | -0.722 | -0.089 | 0.024 |
| Dye 6 | -0.054 | -0.040 | -0.047 | 0.129 | -1.345 | 1.780 | -0.045 | -0.038 |
| Dye 7 | -0.222 | -0.123 | -0.039 | -0.037 | -0.084 | -0.019 | 1.154 | -0.112 |
| Dye 8 | -0.132 | -0.146 | -0.005 | -0.007 | -0.051 | -0.002 | -0.330 | 1.000 |

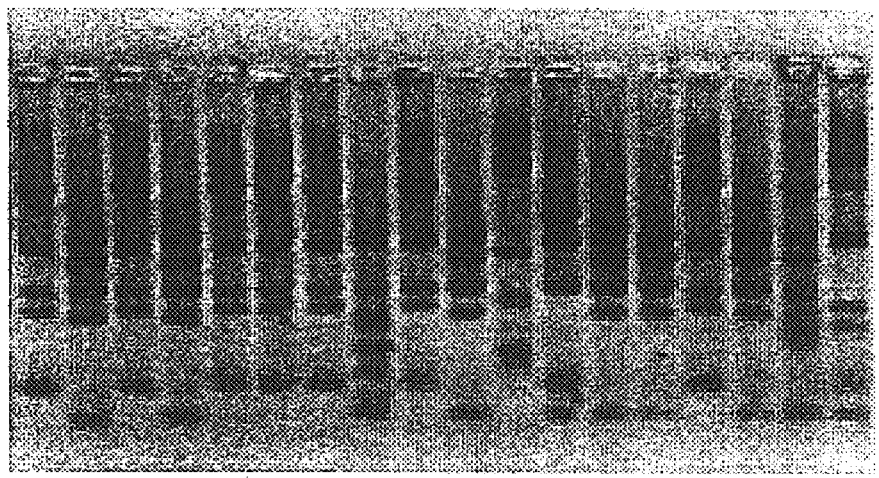
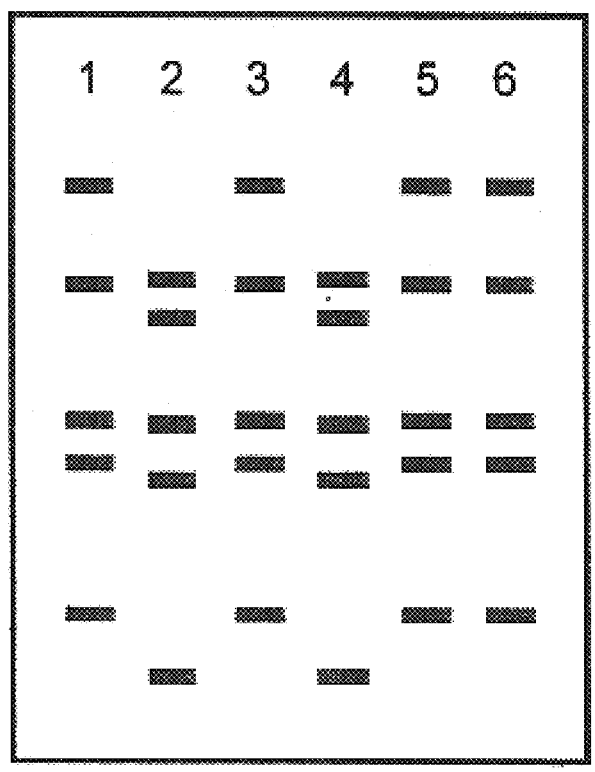
Figure 10

```
E. coli based phylogenetic 16S sequence alignment (positions 305-322):

G A C C A G C C A C A C U G G A A C    E. coli (0)
G A C C A G C C A C A C U G G G A C    C. vinosum (1)
G A U C A G C C A C A C U G G G A C    R. capsulatus (2)
G A U C G G C C A C A C U G G G A C    B. subtilis (3)
G A U C A G C C A C A C U G G G A C    Synechococcus PCC 6301 (2)
G A C C G G G C A G A C U G G G A C    C. aurantiacus (4)
G A G C C C G G A G A C G G A A U C    H. halobium (9)
```

Figure 15

| Probe Sequence | Species Specificity / Phylum or Subdivision | Channel | Color Code | Dye |
|---|---|---|---|---|
| CCACTGCCTTTTACACCAGA | Lactococcus lactis/ Low G+C gram positive | 1 | | Alexa 350 |
| AACTTTACTCCCTTCCTCC | Escherichia coli/ γ Proteobacteria | 2 | | Pacific Blue |
| CCGCGGC(T/G)GCTGG | All (Universal) | 3 | | Bodipy493/503 |
| GCCCTTTGTTCTGT | Bacillus subtilis/ Low G+C gram positive | 4 | | Bodipy R6G |
| ACCGCCCCAAAAGGAGAAACCACA | Arthrobacter globiformis/ Actinobacteria | 5 | | Bodipy 564/570 |
| ACCAGTTGACATCGTTTAGGGC | Leptothrix discophora/ β Proteobacteria | 6 | | Bodipy 581/591 |
| ATCCAGGTACCGTCACCTTAA | Corynebacterium flavescens/ Actinobacteria | 7 | | Cy5 |
| ACAACCCATAGGGCAGTCT | Flexibacter maritimus/ *BCF | 8 | | Cy5.5 |

*BCF is the *Bacteroides, Cytophagales, Flavobacterium* phylum.

Figure 18

|  | Channel 1 | Channel 2 | Channel 3 | Channel 4 | Channel 5 | Channel 6 | Channel 7 | Channel 8 |
|---|---|---|---|---|---|---|---|---|
| Fluorescent Dye | Alexa 350 | Pacific Blue | Bodipy 493/503 | Bodipy R6G | Bodipy 564/570 | Bodipy581/591 | Cy Dye 5 | Cy Dye 5.5 |
| Excitation Filter | 365/30 | 420/20 | 490/10 | 530/10 | 560/10 | 590/10 | 630/10 | 680/10 |
| Dichroic Filter | 400DCXU | 450DCXU | 500DCXU | Q545LP | Q578LP | Q608LP | 645DCXU | Q690LP |
| Emission Filter (CVIF) | 442 nm | 465nm | 520nm | 555nm | 585nm | 615nm | 665nm | 700nm |

Figure 19

|       | Channel 1 | Channel 2 | Channel 3 | Channel 4 | Channel 5 | Channel 6 | Channel 7 | Channel 8 |
|-------|-----------|-----------|-----------|-----------|-----------|-----------|-----------|-----------|
| Dye 1 | 270       | 89        | 31        | 51        | 109       | 35        | 111       | 40        |
| Dye 2 | 155       | 398       | 31        | 46        | 119       | 38        | 125       | 41        |
| Dye 3 | 84        | 84        | 656       | 93        | 127       | 41        | 134       | 39        |
| Dye 4 | 84        | 83        | 52        | 959       | 219       | 63        | 139       | 58        |
| Dye 5 | 90        | 90        | 44        | 181       | 1129      | 451       | 165       | 27        |
| Dye 6 | 80        | 80        | 50        | 75        | 853       | 1910      | 208       | 89        |
| Dye 7 | 91        | 83        | 40        | 68        | 155       | 85        | 2563      | 300       |
| Dye 8 | 94        | 103       | 28        | 52        | 144       | 66        | 888       | 2903      |

Figure 20

|  | Channel 1 | Channel 2 | Channel 3 | Channel 4 | Channel 5 | Channel 6 | Channel 7 | Channel 8 |
|---|---|---|---|---|---|---|---|---|
| Dye 1 | 12.287 | -2.340 | -0.371 | -0.328 | -0.820 | 0.050 | -0.302 | -0.087 |
| Dye 2 | -4.441 | 8.172 | -0.136 | -0.056 | -0.400 | 0.026 | -0.162 | -0.032 |
| Dye 3 | -0.789 | -0.592 | 4.369 | -0.290 | -0.290 | 0.017 | -0.126 | -0.018 |
| Dye 4 | -0.501 | -0.362 | -0.166 | 3.070 | -0.508 | 0.043 | -0.077 | -0.036 |
| Dye 5 | -0.457 | -0.347 | -0.079 | -0.496 | 3.212 | -0.722 | -0.089 | 0.024 |
| Dye 6 | -0.054 | -0.040 | -0.047 | 0.129 | -1.345 | 1.780 | -0.045 | -0.038 |
| Dye 7 | -0.222 | -0.123 | -0.039 | -0.037 | -0.084 | -0.019 | 1.154 | -0.112 |
| Dye 8 | -0.132 | -0.146 | -0.005 | -0.007 | -0.051 | -0.002 | -0.330 | 1.000 |

Figure 21

| Probe Sequence | | Channel | Color Code | Dye | Target Organisms |
|---|---|---|---|---|---|
| CCCATGACAGGCCACTGGCT | (1434) | 1 | | Alexa 350 | *Corynebacterium coyleae* group and prostatitis clone MTcory 3P |
| CCCTCACAGGCTCGCAGACGC | (1253) | | | | |
| CCCTCACAGGATCGCACACG | (1253) | 2 | | Pacific Blue | Uncultured *Corynebacterium* sp. prostatitis clone MTcory21R |
| CAATCGCATCCAAACAATTGTC | (174) | | | | |
| CTGAGCCA(A/C)GATCAAACTCT | (8) | 3 | | Bodipy 493/503 | All Bacteria |
| GGACGGTGCCGTGAATATCCGG | (175) | 4 | | Bodipy R6G | Uncultured *Corynebacterium* sp. prostatitis clone MTcory11W |
| CCCGAAGTGAAAGGCAGATC | (130) | | | | |
| CCACGAGCTCATCTTGCACC | (220) | 5 | | Bodipy 564/570 | Uncultured *Corynebacterium* sp. prostatitis clone MTcory1P |
| CAAGCTGATAGGCCACGAGC | (246) | | | | |
| GTTAAGCACGCCGCCAGCGTTC | (52) | 6 | | Bodipy 581/591 | *Corynebacterium* sp. and related genera |
| TTGTTACGACTTCGTCCCAATCGCC | (1479) | | | | |
| GCCGTGGCTTTCTGATTAGG | (488) | 7 | | Cy5 | *Staphylococcus* sp. (genus specific) |
| CGCACATCAGCGTCAGTTA | (747) | | | | |
| GATTAGCTTGCCGTCACCGG | (1250) | 8 | | Cy5.5 | *Streptococcus* sp. (genus specific) |
| CATGGAATTCCACTCTCCCC | (660) | | | | |

FIGURE 22

| Probe Sequence | Species Specificity / Phylum | Channel | Color Code | Dye |
|---|---|---|---|---|
| GAGACCCGCCTTCGCCACCG<br>CAAGCTGATAGGCCGCGGGC<br>GGCTTCGGGTGTTTACCGACT<br>TTGTTACRRCTTCGTCCCAATCGCC | Actinobacteria | 1 | ■ | Alexa 350 |
| CAATCTCTCAATCCGCCTAG<br>TAGAGTTCCCACCCTAAGTG<br>CTCAGTCCCAGTGTTGGCGG | Chlamydia | 2 | ■ | Pacific Blue |
| CCGCGGC(T/G)GCTGG | All "universal" | 3 | ■ | Bodipy 493/503 |
| CGCGCGCTTTACGCCCAATA<br>GCTTGCCACCTACGTATTAC<br>GCTGCTGGCACATAGTTAGC | Low G+C gram positive | 4 | ■ | Bodipy R6G |
| ACAACCATGCAGCACCTT<br>CGGCACGAGCTGACGACAAC | BCF | 5 | ■ | Bodipy 564/570 |
| GACTTGCATGCTTAAGACGC<br>AGCTGCTGCCTCCCGTAGGA<br>GCGAGCATAAGTCCCCAGGCG | Spirochetes | 6 | □ | Bodipy 581/591 |
| CAGTCCCCTTGTGGCCGTTC<br>CGTGCACACAGAATTGCTGG | Fusobacteria | 7 | ■ | Cy5 |
| GCCCATTGTCCAATATTCCC<br>GCTTTACGCCCAGTAATTCC<br>ACAGCCATGCAGCACCTGTC<br>GAGTACAAGACCCGGGAACG | Proteobacteria | 8 | ■ | Cy5.5 |

FIGURE 23

MULTISPECTRAL TAXONOMIC IDENTIFICATION

RELATED APPLICATION DATA

This application claims the benefit of U.S. Provisional Application No. 60/137,458, filed Jun. 4, 1999, the entire disclosure of which is herein incorporated by reference.

GOVERNMENT LICENSE RIGHTS

This invention was made with Government support under R43GM60209-01 awarded by the NIH. The Government has certain rights in the invention.

BACKGROUND OF THE INVENTION

Identification of microbes (such as bacteria, archaea and simple eucarya) using DNA and other hybridization probes has become increasingly sophisticated and accurate as probe technology and methods have improved. Probes are molecules that bind with high affinity and specificity to target molecules. Up to now, instrumentation for detecting fluorescently-labeled or other spectroscopically identifiable probes has not been able to fully exploit the capabilities of such molecules to identify in situ highly complex (i.e., genotypically or phenotypically diverse) mixtures of biological cells and viruses. Positive identification of single variant organisms in large populations of similar cells is also problematic. Fluorescent and other spectroscopically identifiable labeling methods are ultimately limited by the number of different spectral 'fingerprints' that can be distinguished by the imaging system that is used to measure and sort them. We have created probe sets labeled with as many as eight distinct fluorophores for simultaneous hybridization against 16S small subunit RNA and other targets. These fluorophores are all organic dyes with relatively broad absorption and fluorescence emission bands; however, newly developed inorganic fluorescent quantum dots or nanocrystals (with narrower fluorescence emission bands) can also be used. KAIROS has developed instrumentation and spectral deconvolution and sorting algorithms to increase the number of spectroscopically identifiable tags that can be simultaneously distinguished, thus enabling accurate 'fingerprinting' of bacteria, archaea and eucarya. We have applied these libraries of probes and the spectral deconvolution software to correctly identify highly complex mixtures of cells in situ by spectral sorting. This new technology for multispectral taxonomic identification (MTID) will benefit clinical and environmental microbiology as well as biotechnology. This instrumentation can also be used with other types of multispectral probes, such as fluorescently labeled antibodies.

Identification of microorganisms, eucaryotic cells, and viruses by a variety of methods has become an essential diagnostic tool in areas such as healthcare, food and water quality testing, and enzyme discovery (Amann et al., 1992; O'Hara et al., 1993; Vandamme, E. J., 1994; Birnbaum et al., 1994; Vandamme, P., 1996; Relman, 1998; Schrenk et al., 1998). Identification is an integral part of biological taxonomy, or the classification of organisms. Its medical uses include confirming bacterial serotypes for epidemiological studies (Birnbaum et al., 1994) and monitoring of nosocomial infection (Andersen, 1995). Environmental uses include analysis of water, soil and air, as well as bioremediation monitoring (Schrenk et al., 1998) and studies of population ecology and bacterial phylogenetics (Pace et al., 1986; Ward et al., 1992; Amann et al., 1995). In biotechnology, taxonomic identification can be used for biodiversity screening, bioprocess monitoring and genomic analysis (Amann et al., 1992; Hoheisel, 1997; Head et al., 1998). Traditionally, microbiologists performing bacterial identification have relied on cultivation of organisms, despite the realization that most of them (>99%) are not cultivable by standard methods (Amann et al., 1995; Pace, 1997; Head et al., 1998; Hugenholtz et al., 1998b). Many of these culture-based methods rely on chemical analysis of phenotypic characteristics. For example, there are numerous phenotype-based systems for identifying bacterial and archaeal cultures according to their cellular fatty acid ester content (Osterhout et al., 1991), endogenous enzyme activity and/or antibiotic resistance patterns (O'Hara et al., 1993), and antigenic markers (Porter et al., 1993). In the case of antigenic markers, fluorescently labeled antibodies can be used to specifically identify bacterial serotypes, such as the common food pathogen, E. coli 0157:H7 (Restaino et al., 1997; Seo & Frank, 1999). This technique is useful for accurately identifying microorganisms at the species and subspecies level. Recent advances in combinatorial mutagenesis and phage-display technology have also made it possible to create peptides and proteins that have the affinity and specificity of antibodies but are not derived from antibody molecules per se.

More recently, molecular based methods have been developed to examine he diversity of microorganisms without the need to isolate or culture them. One class of methodology takes advantage of the conserved nature of protein synthesis in all cellular organisms. With about 10,000 partial or complete sequences now available for comparison, the small subunit ribosomal RNA (rRNA) (which contains the 16S rRNA in bacteria and archaea and the 18S rRNA in eucarya) is currently the molecule of choice for identifying organisms at the species level. Other rRNA targets include the large subunit 5S or 23S rRNA (in bacteria and archaea) and the large subunit 5S, 5.8S and 28S rRNA (in eucarya). Molecular strategies based on PCR, cloning, sequencing, and probing have enabled biologists to examine the total microbial community in a sample without any a priori knowledge of the species present in the mixture (Amann et al., 1995). Although rRNA-based identification is only accurate to approximately the level of species, its tremendous versatility makes it extremely valuable for high-throughput screening and identification of microorganisms.

The information gained from 16S/18S rRNA sequence comparisons can be used to deduce detailed phylogenetic relationships based on evolution. An evolutionary distance map generated from 16S rRNA sequence data highlights the major lineages of Bacteria and Archaea (FIG. 1). The highly conserved portions of 16S/18S rRNA are ideal for designing primers that will amplify 16S/18S rRNA genes from all three domains of life (Bacteria, Archaea, and Eucarya). At the other extreme, primers can be designed to highly variable regions of 16S/18S rRNA and thus amplify only a particular species or genus in a mixture of microorganisms. Likewise, fluorescent DNA hybridization probes based on 16S/18S sequencing information can be constructed to identify organisms in a large group (i.e., phylum) or in a localized group (i.e., genus), depending on whether the probe sequence is complementary to a conserved or variable region of the 16S/18S rRNA, respectively. Ribosomal RNA is a particularly convenient and attractive hybridization target for quantitative microscopy because a typical E. coli cell contains approximately 20,000 ribosomes (Neidhardt, 1987), and thus ~20,000 copies of the target sequence. These probes can also be made using polymers other than DNA. Such polymers include RNA as well as nucleic acid analogues, such as peptide-nucleic acids, phosphorothioates, and morpholinos. Probes can be covalently labeled with fluorophores or other spectroscopically identifiable labels to enable in situ hybridization and identification by fluorescence or other spectroscopic imaging microscopy (Amann et al., 1990). The probes can also contain fluorophores designed to be FRET (fluorescence resonance energy transfer) pairs, such as molecular beacons.

PCR has been an extremely powerful tool for analyzing samples and constructing databases of sequences. It has been used to amplify the 16S-rDNA genes from microorganisms isolated from highly diverse and extreme environments, as well as from clinical sources (Hugenholtz et al., 1998b; Relman, 1998). Unknown organisms are being identified at the level of new phyla, expanding on the bacterial line of descent. Many of these new phyla do not have cultured representatives, and yet PCR analysis indicates that they are abundant in the environment. These organisms are completely novel, and they may be a rich source of new antibiotics, enzymes, and other bioactive compounds for medicine and biotechnology (Short, 1997). Recently, attempts have been made to reduce the sequencing load and to increase the screening throughput by employing restriction fragment length polymorphism (RFLP) analysis to examine the diversity of these microbial populations. To design actual probes however, a full length 16S rRNA sequence is needed, and it must be aligned into an existing database. The methodologies for bacterial identification by molecular techniques are outlined in FIG. 2.

As we noted above, the etiology of human infections has historically relied on cultivation to identify the responsible microorganisms. Isolation and inoculation of cultured microbes is the conventional means to link causation of disease to a particular pathogen. However, microbes that are difficult or impossible to culture with present techniques can cause some human clinical syndromes that were originally thought to be nonmicrobial. Indeed, a number of pathological conditions are known to be the result of uncultivated bacteria (Fredricks & Relman, 1996; Lorber, 1996). A few examples using molecular methods to identify uncultured bacteria have been reported. The causative agent of Whipple's disease, for instance, is resistant to culture, but could be identified using PCR and 16S ribosomal RNA sequence analysis (Relman et al., 1992). Additionally, the PCR approach has been used to identify the Whipple bacillus (*Tropheryma whippelii*) in the eye and mononuclear cells of blood (Rickman et al., 1995; Müller et al., 1993). Similarly, the etiologic agents of cat scratch disease and bacillary angiomatosis were identified using PCR-based technology and 16S rRNA analysis (Adal et al., 1994). Sequence analysis identified the agent as a member of the genus Rochalimaea (Proteobacteria; alpha subdivision).

The difficulty of cultivation has also led to the realization that many human infections are more complex than originally thought. The common expectation of syntrophy, where one organism is dependent on the metabolism of another—frequently observed in the environment—may be prevalent in the diseased state as well. Biofilms are a good example of microbial communities, and they have caught the attention of biomedical science, since microbial communities existing as biofilms play a role in both human health and disease. Bacteria that form these biofilms are well known in tooth decay and artificial implants, and are now implicated in other diseases, including kidney, urinary tract and ear infections. Individual species of bacteria in a community may be dependent on other species for survival, which makes isolation in culture a formidable task. Likewise, analyzing such communities in situ using the currently available methods is a difficult undertaking.

Evidence for a complex bacterial population in a disease condition was recently described for prostatitis, a common disease in adult men of all ages (Tanner et al., 1999). Frequently, patients are diagnosed with "nonbacterial" prostatitis, but some of these patients respond to antibiotic treatment and show evidence of distinct bacterial species by molecular techniques, despite the absence of cultivable bacteria (Tanner et al., 1999). These species were identified by phylogenetic analyses of their 16S rRNA gene sequences from mixed populations. Prostatitis is an appropriate model to study bacterial identification by mTID imaging because various bacterial species are present, including some that are uncultured, and samples are easy to acquire and process. A second disease amenable to study by MTID is bacterial vaginosis, a prevalent disorder that is probably the result of an imbalance in the various bacterial populations that comprise the vaginal flora. Interestingly, biofilms may play a significant role in the pathology of prostatitis and vaginosis, contributing to the lack of cultured microorganisms in many patients (Potera, 1999).

In addition to PCR/RFLP analysis, other molecular techniques, such as random amplified polymorphic DNA-PCR (RAPD-PCR; Williams et al., 1990) or arbitrarily primed-PCR (AP-PCR; Welsh & McClelland, 1990), DNA or RNA sequencing (Rappé et al., 1998), denaturing gradient gel electrophoresis (DGGE; Muyzer & Smalla, 1998), and micro-array analysis (Dubiley et al., 1997; de Saizieu et al., 1998) can be used to identify microorganisms. However, most of these are not usable by themselves for in situ analysis.

For in situ analysis of these bacterial species, the information gained from PCR and sequencing can be advantageously exploited to synthesize fluorescently labeled or other spectroscopically identifiable oligonucleotide probes for direct hybridization against the 16S rRNA. Up to now, however, these in situ hybridization experiments have utilized no more than one or two probes per sample because of the lack of adequate instrumentation to handle sets of probes that are labeled with fluorophores emitting at several different wavelengths. Moreover, software is not available to design different probes that all have nearly the same melting temperature. The ability to employ multiple probes simultaneously and to analyze them with a calibrated system increases the amount of information that can be obtained from a given sample and substantially increases the overall throughput. In addition, the analysis can be performed on single cells, without extracting, purifying, and amplifying the nucleic acids each time. A whole-cell in situ method such as MTID has numerous advantages over other bacterial identification techniques, including:

Unculturable organisms can be detected

Cells need not be viable

DNA/RNA amplification is not necessary after the sequence is known

Processing is rapid

High throughput is achievable

Unknowns can be tentatively identified via phylogeny

Single cells can be individually analyzed

Rare cells can be detected in complex backgrounds

Once the PCR-based analyses have enabled species-specific hybridization probes for known populations of bacteria (FIG. 2), one can take full advantage of the speed and simplicity of a spectroscopic-based method (i.e., MTID)

to streamline the process. Moreover, even if sequence-information is lacking, MTID still enables a level of identification that becomes increasingly accurate as more spectroscopic channels are used to quantitate the hybridization levels of the targeted probes. Unlike identification that is based solely on PCR, MTID is a highly parallel, imaging-based technique that enables in situ analyses and identification of many individual cells within a single field of view.

Due to the fact that greater throughput and increased accuracy of identification can be achieved by using multiple probes, we have chosen to apply the techniques first described for multicolor fluorescence in situ hybridization (FISH) (used in chromosome painting; Schröck et al., 1996; Speicher et al., 1996) for taxonomic identification. There are two methods for actually labeling the probes. For example, in the 'ratio labeling' technique (Nederlof et al., 1992), various fluorescent dyes are combined in specific proportions on each probe. In this case, the relative emission intensity of each dye is used to generate a spectral fingerprint to identify the probe. Thus, the maximum probe complexity (C) is given by the expression $C=L^D-1$, where L is the intensity level of the fluorescence emission for each fluorophore and D is the number of different dyes. The simplest variant of this, known as the 'combinatorial' approach (Ried et al., 1992), uses only two 'levels' (i.e., 'on' or 'off') to generate the colors. In this case, $C=2^D-1$. For five different dyes, this scheme is capable of generating probes of 31 different colors, or enough spectral diversity to assign a unique color to each of the 24 human chromosomes for automated karyotyping. However, since the number of microbial species is very large, a five-channel system is insufficient to cover the complexity. Nevertheless, there are only a few published examples in which even two dyes have been used simultaneously for bacterial identification (Amann et al., 1990; Wallner et al., 1993; Gunderson & Goss, 1997), and at the present time no one has yet taken full advantage of FISH/SKY technology for three or more fluorophores for bacterial or other taxonomic identification. This is why we developed an eight-channel MTID imaging system with accompanying software for automated spectral deconvolution, sorting, and classification, as well as software and protocols for highly multiplexed probe design, labeling, and hybridization.

BRIEF DESCRIPTION OF THE DRAWINGS

The file of this patent contains at least one drawing executed in color. Copies of this patent with the color drawings will be provided by the Patent and Trademark Office upon request and payment of the necessary fee.

FIG. 10 Restriction fragment length polymorphism analysis of 16S rDNA clones from samples of expressed prostatic secretions (EPS). The top image (A) is of an agarose gel of 16S rDNA digested with MspI and HinP1I. The bottom schematic (B) indicates two distinct RFLP patterns found in the first 6 lanes. Identical patterns represent the same species or closely related species.

FIG. 15 Phylogenetic sequence alignment for identifying seven different organisms. The sequence alignment compares the various 16S sequences from the 7 organisms listed to demonstrate how, for this particular sequence region, the number of mismatches (in parentheses) roughly correlates with the calculated phylogenetic distance from *E. coli*. An antisense oligonucleotide based on the *E. coli* sequence is therefore a candidate for a phylogenetic probe. Mismatches are shown in bold. Locations are given using the *E. coli* 16S numbering. Sequences are given 5'→3'.

FIG. 18 Probe sequences and their corresponding target organisms. The numbers in parenthesis refer to the 16S rRNA sequence position relative to *E. coli* 16S rRNA.

FIG. 19 Optimization of MTID filter parameters to an 8-dye set.

FIG. 20 [G] matrix comprised of the background-subtracted (group average) grayscale values derived from FIG. 8 and applied in FIGS. 7, 8, and 9.

FIG. 21 [C] matrix derived from FIG. 8 and used in FIGS. 7, 8, and 9. Coefficients within boxes that are not highlighted have less than a 10% effect on a channel's overall correction.

FIG. 22 Probe sequences and their corresponding target organisms. The numbers in parenthesis refer to the 16S rRNA sequence position relative to *E. coli* 16S rRNA. Probe set is illustrative of a set useful for analysis of prostatitis samples.

FIG. 23 Probe sequences directed against the 16S rRNA of seven bacterial phyla that are known to contain pathogenic species. Probe set is illustrative of a set useful for taxonomic analysis of unknown samples.

SUMMARY OF THE INVENTION

Figure 1:
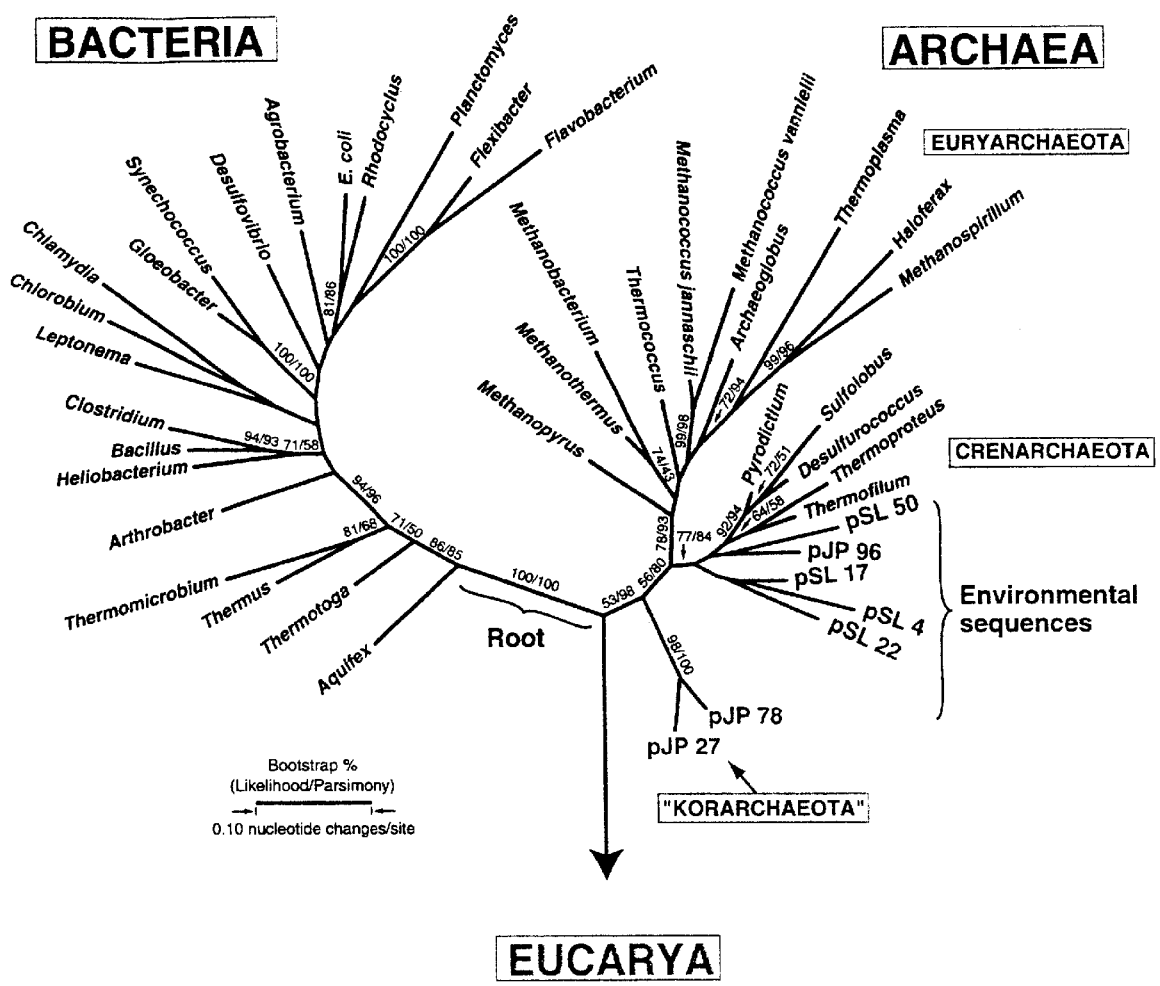
FIG. 1 Phylogenetic tree of the three domains of life (Bacteria, Archaea, and Eucarya) based on the evolutionary distance of the 16S/18S rRNA molecule (adapted from Barns et al., 1996). Members of the Eucarya are omitted for clarity. The genera listed are representative of major lineages of the two domains. Bootstrap values indicate the percentage of trees that resulted in the branching order shown. Two different treeing algorithms, maximum likelihood and maximum parsimony, generated these values. Environmental sequences are known only from their 16S rRNA gene. Note that although the arrangement of the branches on the tree may change as new information is gathered, this does not affect the accuracy of using a unique 16S rRNA sequence to identify a particular organism.

The invention provides an instrument for imaging and analyzing biological cells, particularly those of bacteria and archaea, in complex populations of microorganisms. The instrument includes a light source for controllably emitting light having a selected set of wavelengths; a movable set of dichroic mirrors for a selected set of wavelengths; a variable filter or set of filters for spectrally selecting light imaged by the camera; a camera, for imaging light received from the target within a selected set of wavelengths; and a processor, coupled to the light source, the turret containing the dichroic mirrors, the variable filter or set of filters, and the camera, for controlling the wavelengths of light emitted from the light source, the position of the dichroic mirrors, the wavelengths of light imaged by the camera, and the analysis of the data. The instrument automatically images the target, obtains calibrated images at multiple wavelengths, and automatically indicates the fluorescence or other spectrally identifiable signals for each pixel at the selected wavelengths.

The invention also provides a method for imaging and analyzing populations of target cells. Included is a method for empirically calibrating an optical system, the method comprising the steps of collecting data for calibration in a matrix [G], in which the columns of the matrix represent spectral channels, and the rows of the matrix represent spectral groups, solving for a correction matrix [C], collecting vector data [Y] of pixel intensities from uncalibrated images, and correcting [Y] by matrix multiplication with [C] to obtain vector [X] of pixel intensities for calibrated images empirically calibrated vectors [X] for the pixels in the calibrated image.

Also included is a method for empirically correcting images of cells that are obtained through the use of multiple spectral tags. The method includes the steps of selecting a probe that binds to a target cell used for calibration, dividing a sample of target cells into aliquots, dividing a sample of probe solution into aliquots, labeling each aliquot of probe solution with a different spectral tag to generate a set of labeled probe solutions, mixing aliquots of the labeled probe solutions with aliquots of target cells to generate a set of probe-labeled target cells, mixing together approximately equal proportions of probe-labeled target cells, acquiring images of the mixed probe-labeled target cells at multiple wavelengths, calculating a correction matrix for each labeled probe set, and applying the correction matrix to images of unknown cells to correct the image of the unknown cells.

The target cells can be analyzed based on multiplexed, fluorescently labeled oligonucleotide probes hybridized to ribosomal RNA (rRNA) or chromosomal DNA. They can also be analyzed based on multiplexed, fluorescently labeled antibodies. For the rRNA hybridization probes, a computer algorithm has been written to find a set of probes whose melting temperatures are approximately identical. Differences in ribosome number among the cells are corrected by using a fluorescent probe that binds to all known target sequences. The invention uses the imaging data to automatically classify the cells. It can further be used to image and classify cells whose DNA or RNA has been selectively amplified by in situ PCR. In this case, the amplified product can be directly labeled via incorporation of fluorescent nucleotides, or it can be labeled indirectly by probing the amplified product with antibodies. The problem of spectral overlap among the fluorophores is corrected by calibrating the system with known, fluorescently labeled standard cells.

The invention further provides sets of probes that target specific taxonomic groups based on sequence information obtained from the sample. Here, a taxonomic group is defined as a useful grouping of species, which, for the purposes of efficient identification, can be adjusted by the user. Thus, it not only includes the traditional taxa, such as "division" or "species," but also functional groupings, such as "pathogens" or "unculturables." This information can be used to design probe sets that cut across traditional boundaries to identify, for example, bacteria from multiple divisions that contain known pathogens or unculturable species. In this way, probe sets can also be targeted to identify organisms associated with particular disease states, such as prostatitis and vaginosis. They can also be used to monitor bacteria for other clinical analyses and diagnoses. More generally, probe sets can be designed so that the spectral fingerprints reflect the phylogeny of, for example, all bacteria and archaea. These can be used to identify complex populations of unknown microorganisms. Methods are also described for rapidly obtaining information about the overall genetic diversity within the sample. This information is useful for evaluating environmental samples for bioremediation or for shotgun genomic cloning during bioprospecting. Included in this aspect of the invention is a method for taxonomic identification of an organism. The method includes the steps of hybridizing at least one probe to an organism, quantifying the resulting first hybridization signal, hybridizing the probe to at least one reference organism, also referred to as a benchmark organism, quantifying the resulting second hybridization signal, and taxonomically identifying the organism by calculating the difference between the second and first hybridization signals, wherein the difference increases with increasing taxonomic distance between the organism and the benchmark organism.

DETAILED DESCRIPTION OF THE PREFERRED EMBODIMENTS

The present invention provides an instrument and methods for high-throughput in situ identification of biological cells in complex populations. The instrument is a new fluorescence imaging microscope system that performs multispectral taxonomic identification (MTID). Use of the instrument and associated methods for probe design and binding can improve:

the analysis and diagnosis of infectious diseases the monitoring of air, water, soil and food for contamination the discovery of new enzymes and antibiotics the development of microorganism-based fermentation and bioprocessing the study of biofilms and biological consortia It has been estimated that over 99% of all known microorganisms are uncharacterized and unculturable. We have developed an integrated system of fluorescent probes and multispectral microscopy techniques to correctly identify unknown and unculturable microorganisms based on their RNA or DNA sequences. This process includes probe design, hybridization, imaging, image analysis, and spectral analysis. This system can also be employed to identify such targets using fluorescently labeled antibodies and in situ PCR (polymerase chain reaction) amplification.

Commercial opportunities for the use of the MTID system include clinical diagnostics, public health, industrial enzymes, drug discovery, and chemical and food processing. As new organisms with new properties are discovered, there will be an increasing demand for identification technology to study the remaining unknown species.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

All publications, patent applications, patents, and other references mentioned herein are incorporated by reference in their entirety. In the case of conflict, the present application, including definitions, will control. In addition, the materials, methods, and examples described herein are illustrative only and not intended to be limiting.

Other features and advantages of the invention will be apparent from the following detailed description, the drawings, and from the claims.

Instrument and Software

Figure 3:
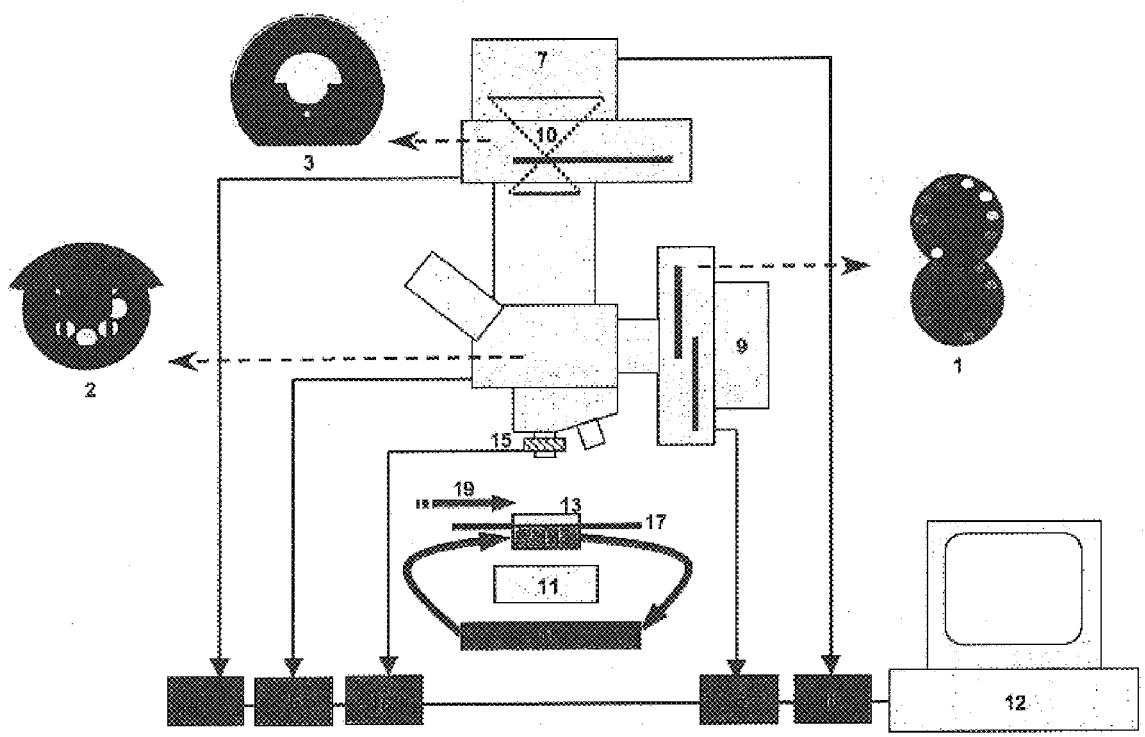
FIG. 3 Schematic of the MTID instrument. All three principal light-filtering devices are shown in this figure, including: 18-position filter wheel (1) for selecting the wavelength of the light used to illuminate the sample, 8-position dichroic turret (2), and the Circular Variable Interference Filter (CVIF, 3). These filters are positioned by stepper, motors that are computer-interfaced via serial controllers (4, 5, and 6), while the CCD camera (7) uses a parallel computer interface (8). Light source (9) is used in epifluorescence, where the dichroic mirrors mounted within the dichroic turret (2) act to reflect short wavelength (narrow band excitation) light down to the sample while transmitting longer wavelength (fluorescent) light up to the CVIF (3) and CCD (7). The CVIF enables sub-pixel image registration and its use at the narrowest waist in a post-objective light path (10) is patented by KAIROS (U.S. Pat. No. 5,852,498). Also shown are an objective heater (15), that optionally can be computer-interfaced via a serial controller (16). Slide (13) is mounted on microscope stage (17), optionally outfitted with a heat sink (14), liquid nitrogen circulator (18), and a nozzle emitting a dry nitrogen stream (19) for cooling the slide. Optional light source (11) can be used for transillumination of the slide. MTID instrument, data acquisition and data analysis are controlled by computer (12).

The invention provides an instrument for imaging and analyzing biological cells, particularly those of bacteria and archaea, in complex populations of microorganisms. The instrument is illustrated in FIG. 3. It includes a light source (9) and an 18-position filter wheel (1) for selecting the wavelength of the light used to illuminate the sample; a movable set of dichroic mirrors for a selected set of wavelengths (2); a Circular Variable Interference Filter (CVIF) (3) or set of filters for spectrally selecting light imaged by the camera; a camera (7), for imaging light received from the target within a selected set of wavelengths; and a processor (12), coupled to the light source, the turret containing the dichroic mirrors, the variable filter or set of filters, and the camera, for controlling the wavelengths of light emitted from the light source, the position of the dichroic mirrors, the wavelengths of light imaged by the camera, and the analysis of the data.

In an alternative embodiment, the filter wheel (1), dichroic mirrors mounted within the dichroic turret (2), and the CVIF (3) illustrated in FIG. 3 may be replaced with an off-the-shelf device such as the Olympus AX-URBC/8 eight position automated turret that contains 8 excitation filters, 8 dichroic mirrors, and 8 emission filters. The turret may be computer controlled through a computer-to-microscope interface such as the model U-MCB-3-2 manufactured by Olympus. Both the AX-URBC/8 and the U-MCB-3-2 are used to retrofit a microscope such as the Olympus AX70 epifluorescence microscope outfitted with the microscope's standard Xenon, Mercury, or QTH illuminators. All optical filters and dichroic mirrors can be custom installed to the same specifications as given in FIG. 19 by using filters and dichroic mirrors manufactured by Chroma Technology Corp. (Brattleboro, Vt.).

The instrument automatically images the target, obtains fluorescence images at multiple wavelengths, and indicates the fluorescence signal for each pixel at the selected wavelengths.

Although many of the examples of target cells described below are bacteria, the target cells can be composed of any biological cells, including those from the divisions archaea, bacteria or eucarya. Screening such cells in a massively parallel manner in situ has the advantage that rare cells and cells that cannot be cultured can still be identified, since the pixels corresponding to the fluorescence signals from an individual cell can be sorted and grouped. Thus, even a single cell within a large and diverse population of other cells can be distinguished.

One of the most challenging engineering problems in MTID is to spectrally separate and quantitate many different fluorescent tags within a complex mixture while maintaining pixel-resolution (spatial) image registration. In addition, the MTID imaging spectrophotometer requires the spatial resolution of an epifluorescence microscope (<1 nm) and the spectral resolution of a conventional fluorimeter (~5 $\mu$m). To meet these engineering goals, we replaced the fixed-wavelength excitation and emission filters of a conventional epifluorescence microscope (Olympus AX80) with a large number of discrete excitation filters and a fully tunable emission filter, respectively (FIG. 3). This tunable filter consists of a computer-interfaced Circular Variable Interference Filter (CVIF) to select the emission wavelength. This permits the flexibility of choosing any desired wavelength between 400 and 700 nm. Because of the extreme surface parallelism of the CVIF, we have been able to achieve sub-pixel image registration—a result that is not usually achievable with a set of conventional emission filters unless they are permanently mounted using an autocollimator. In addition, signal-to-noise considerations in fluorescence microscopy demand an epifluorescence configuration; therefore, we incorporated a programmable 8-position turret (containing dichroic mirrors) into the MTID instrument. To achieve intense monochromatic illumination, we have also adapted a stepper-driven, dual-wheel excitation filter set (carrying 18 narrow bandpass filters) to the epi-illumination optics of the AX80. A key feature of the optical system is the physical separation of the dichroic mirrors from the-excitation and emission filters. This allows the latter filters to be easily replaced by any device that transmits light having the desired peak wavelengths and bandwidth.

The microscope stage, which is a device for holding the target cells, can be fitted with an optional holder for controlling the temperature of the cells. A cryogenic stage is particularly useful for illuminating the sample at low temperature. Reducing the temperature of the sample, for instance to below approximately 200 K is advantageous for narrowing fluorescence emission bands, thus reducing spectral overlap and improving resolution. This enables one to increase the number of fluorophores that can be simultaneously distinguished. Temperature-regulated stages are available from Linkham Scientific Instruments (Waterfield, U.K.).

Figure 5:
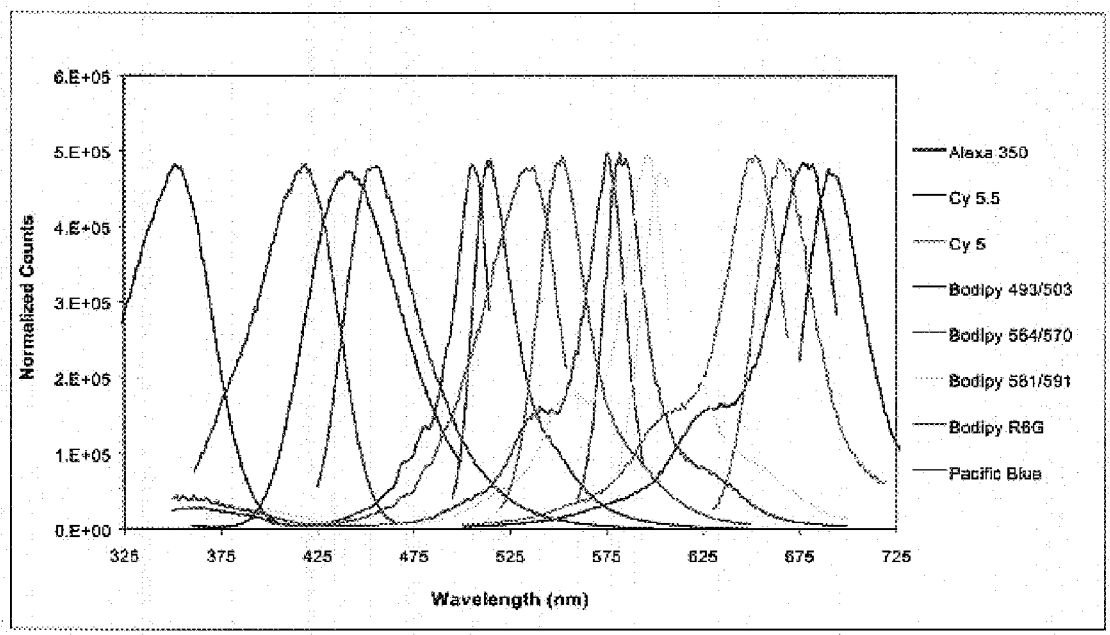
FIG. 5 Excitation and emission spectra for fluorophores. The excitation (left) and emission (right) spectrum of each dye is shown in the same pseudocolor.

Fluorescent dyes were selected (FIG. 5) so as to minimize spectral overlap among channels, provide simple coupling reactions to DNA probes, and maintain high quantum yields with low photodestruction. Each fluorophore/channel combination was optimized with respect to the wavelength of maximum transmission and bandpass for the excitation and emission filters, and the cut-on for the dichroic beamsplitter. Typically, the excitation filter for a particular dye is placed close to the dye's excitation maximum while minimizing the excitation of the next bluest and next reddest dyes. The dichroic filter is set slightly to the blue of the midpoint between the excitation and emission maximum of the dye; while the narrow bandwidth CVIF is positioned as close as possible to the emission maximum. Since signal intensity and spectral differentiation are optimized simultaneously, selected wavelengths can be offset and may not necessarily correspond to a dye's peak maximum.

The optimization of MTID's filters-to-fluorophore set is essential in reducing light dose and photodestruction—as well as spectral overlap. This is in stark contrast to other instruments that are commercially available. On the other hand, our Fluorescence Imaging MicroSpectrophotometer (FIMS) configuration (Youvan et al., 1997) is not optimized for any particular set of dyes as it performs full-spectrum excitation and emission scans. Thus the MTID configuration, using discrete excitation filters, a set of 8 dichroic filters, and a full spectrum CVIF, is unique. Five optical parameters were optimized simultaneously for each channel summarized in FIG. 19: two parameters are specified for each excitation filter (wavelength of maximum transmission and bandwidth); two parameters are specified for each dichroic filter (inflection point of the transmission cut-on and out-of-band light transmission characteristics); one parameter is specified for the wavelength of maximum transmission of the CVIF.

The discontinuous nature of the "channels" involved in the prototype MTID instrument required implementation of additional hardware and software drivers. The MTID prototype utilized three separate serial control interface devices to specify: 1) the illumination wavelength (filter wheel), 2) the selection of a dichroic mirror (8-position turret), and 3) the emission wavelength (CVIF). The second of these three serial controllers also controlled light shutters. A fourth, parallel controller interfaced to the CCD camera, set parameters for pixel binning, dark-frame subtraction, temperature, and exposure time. However, this arrangement can be simplified by multi-threading the filter wheel, turret, CVIF, and CCD controllers within the acquisition software to enable full hardware automation without conflicts. The camera interface can also be upgraded from parallel to Ethernet.

Software running in Microsoft Windows 98 can encounter substantial problems in using multi-threaded MTID software to control serial devices. The major problem arises from limitations in the number of Interrupt Requests (IRQs) available with serial ports and devices that have minimal 'handshaking' standards. Thus, it may be preferable to incorporate USB-to-serial conversion devices. USB requires only one IRQ for up to 127 devices. A USB bus has a bandwidth of 12 Mb/s, and since each of the controllers is very low in its actual frequency of usage, USB is a very suitable "single" connection point for multiple devices. An additional consideration in upgrading the software is to fully enable multitasking, so that it is no longer 'legal' for a single device to interrupt the CPU's clock. This can be done by employing either: 1) a fully compliant IEEE 1284 peripheral interface chip for parallel download, or 2) an Ethernet card built directly into the CCD camera interface. Both of these options are compatible with automated software acquisition using a multi-threaded paradigm. Ethernet (option 2) is ultimately superior because of the reduced download time.

An additional upgrade could involve replacing the camera with a 16-bit, scientific grade, Ethernet-interfaced CCD camera.

Methods for Preparing and Identifying Target Cells

Figure 4:
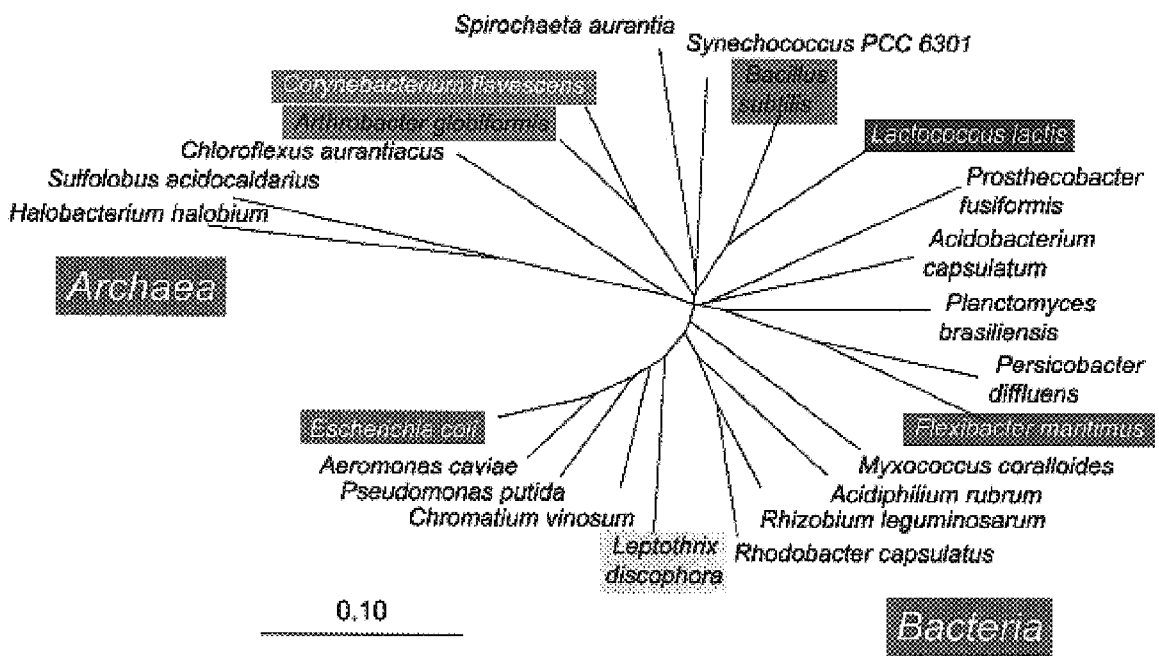
FIG. 4 Bacteria used as test targets. This "unrooted" tree, constructed using ARB, is color-coded to highlight seven different species used in one multispectral experiment described below. The bar indicates 0.1 nucleotide changes per nucleotide sequence position.

After searching the scientific literature and the rRNA phylogenetic databases, we selected a set of approximately two dozen well-characterized, nonpathogenic bacterial and archaeal species that were used in the initial MTID studies. This particular set of species provides diverse 'targets' from many different taxa, including the Archaea, several members of the Proteobacteria, the Low G+C gram-positive bacteria, and Actinobacteria (High G+C gram-positive bacteria). FIG. 4 shows one particular set of seven species that were used in the hybridization experiment shown below. In FIG. 18, we list specific probe sequences and fluorescent dye labels used in this experiment. Sixteen other species-specific probes were designed (including Archaea), and a series of analogous experiments achieved other species-specific identification (data not shown).

With the aid of software KAIROS has developed for iso-$T_m$ probe design, it is possible to design DNA oligonucleotide probes such that the RNA-DNA heteroduplexes have melting temperatures that are identical to within ±2° C. Several different melting temperature equations were evaluated, and the method of Sugimoto et al. (1995) was found to be most reliable. This method utilizes thermodynamic parameters ($\Delta S°$, $\Delta H°$, $\Delta G°$) for 16 nearest-neighbor sets and one initiation factor to predict the stability of RNA/DNA hybrid-duplexes. Other predictive equations were also evaluated, but were found to give disparate and inconsistent $T_m$ values. In addition to critically controlling $T_m$, this newly written software also eliminates probes that have: (1) hairpin structures, (2) overlap between binding sites, (3) target sites with modified bases, and (4) target sites with sequence ambiguities. Differences among rDNA genes, as well as trivial sequencing errors, contribute to these sequence ambiguities.

In addition to the species-specific primers described below, this software is essential for designing more complex probes. For phylum recognition, 'probe ensembles' have been designed that consist of mixtures of up to 10 different oligonucleotides with the same fluorophore label—each ensemble is targeted to sequences representative of a selected phylum. This leads to the interesting concept of differentiating fluorescence intensity levels as a means of "fingerprinting" bacteria, since some organisms within a phylum are expected to have different numbers of nucleotide mismatches with each of the probes in the ensemble. Such quantitative intensity measurements can only be performed on a calibrated instrument.

Monolabeled probes for hybridization are typically made by synthesizing oligonucleotides having a 5' end with an aminoalkyl linker. These are then reacted with dye molecules having an isothiocyanate or succinimidyl ester group and subsequently purified. Other labeling schemes based on direct incorporation of a 5' dye-labeled nucleotide (Glen Research, Sterling, Va.) or sulfide linkages (Vector, Burlingame, Calif.) are also possible. Numerous commercially available fluorophores can be used for this purpose. These include the Amersham dyes Cy2, FluorX, Cy3, Cy3.5, Cy5, Cy5.5 and Cy7, whose emission maxima cover the range from 506 nm to 767 nm, as well as dyes such as Texas Red-X (Molecular Probes, Eugene, Oreg.), which emits at 615 nm, between Cy3.5 and Cy5, and the five BODIPY dyes (Molecular Probes), which emit between 510 nm and 618 nm. Molecular Probes also offers dyes that emit in the blue, such as AMCA and other coumarins. The availability of numerous dyes with reactive linkages makes it possible to select spectrally separated tags that can be imaged in the MTID system.

Whole cell in situ hybridization against rRNA is typically carried out by immobilizing cells on gelatin-coated slides after they have been fixed and permeabilized. The probe solution is then added to the slide and incubated for 2–15 hours at a temperature that is determined by the melting temperature ($T_m$) of the oligonucleotide DNA probe/rRNA duplex. After hybridization, slides are washed and then mounted in an antifade reagent (Amann et al., 1990; DeLong et al., 1989; Rice et al., 1997). To facilitate high throughput of MTID samples, we have also developed a micro-volume hybridization protocol that can be performed in microcentrifuge tubes or microplate trays. This procedure is analogous to conventional methods with the exception that the cells are fixed, permeabilized, hybridized, and washed in suspension. Cells are collected at the end of each step by a brief, low speed centrifugation step. In addition to being more amenable to automation and robotic handling, another advantage of hybridization in suspension is that it prevents the loss of cells, such as coccoid bacteria, which adhere poorly to slides. This is critical for accurately enumerating cells within complex bacterial populations. Micro-volume hybridization is also essential for constructing calibration slides, where it is important to combine bacteria which have been hybridized in separate reactions onto a single slide (see section on calibration).

Figure 6:
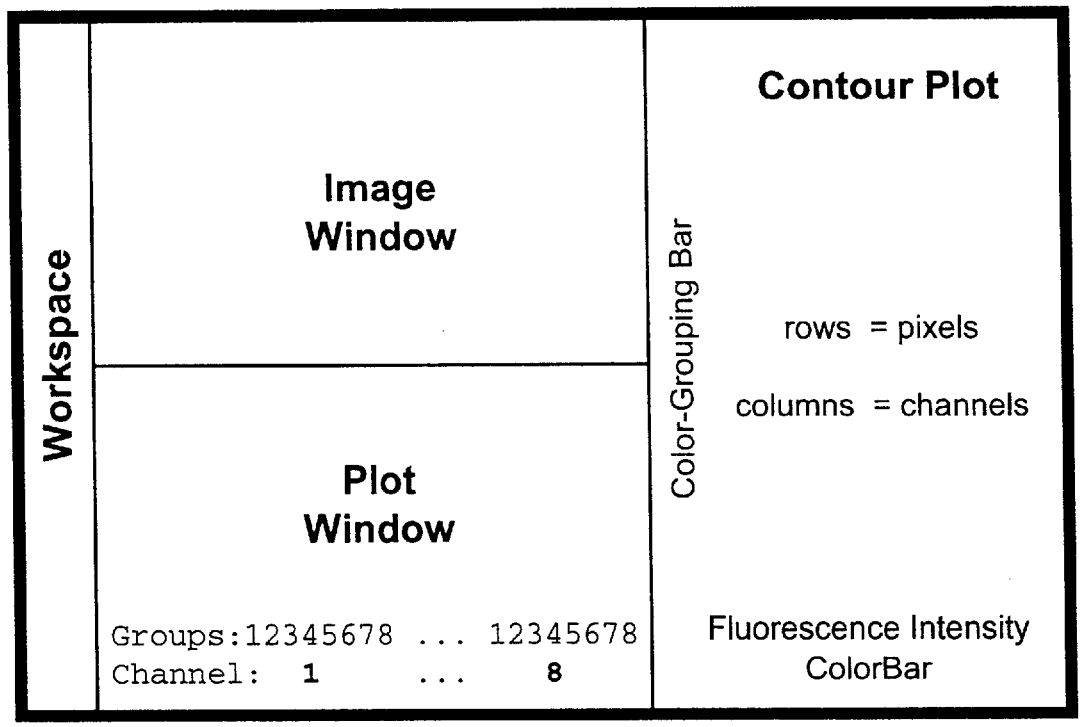
FIG. 6 Schematic of the MTID Graphical User Interface.

The MTID graphical user interface (GUI) includes multiple window types, wizards, and a number of options pertaining to file management, data acquisition, image processing, spectral analysis and display. It is not a simple operation to visualize and extract useful information from massive amounts of multidimensional data. A schematic of the ultimate MTID GUI—which coordinates the display of both spatial and spectral information—is depicted in FIG. 6.

The Workspace Window on the far left is used to organize projects, files, and spectral data. It maintains point-and-click functionality very much like the Microsoft Explorer. An Image Window is provided for the user to display processed images at different magnifications. Traditionally, the Plot Window has been used to display line spectra similar to that of a conventional spectrophotometer. In MTID, we have written code to display histogram or bar-graph style data. To the right, a Contour Plot Window with multiple components is depicted. The Contour Plot was pioneered by KAIROS as a tool to visualize and extract information from as many as 1,000,000 individual spectra simultaneously. In an unsampled display mode, each row of the contour plot corresponds to a single pixel or feature in the image. In MTID, each column of the contour plot corresponds to a spectral channel. The fluorescence intensity of the feature in that spectral channel is encoded by a scheme that is defined by the horizontal ColorBar directly below the Contour Plot. Accordingly, fluorescence intensities are color encoded using black for the lowest intensity and a rainbow of warmer hues to depict higher fluorescence intensity values, while reserving white for highest intensity. All three windows are interactive, and mappings between the windows are maintained via the vertical "Color-Grouping Bar". For example, clicking on a single row in the Contour Plot results in the appearance of a colored tick mark next to this row while simultaneously updating the Plot Window and highlighting the associated feature in the Image Window—all using the same 'marking' color. Clicking on a different row while holding the Ctrl key down, displays corresponding information for this second feature in a different color so that different spectra can be compared. Multiple rows can be associated into a color group by dragging the computer's mouse down the side of the Contour Plot, thereby invoking a different color for each group selected.

For condensing and visualizing massive amounts of spatial and spectral information, algorithms associated with menus 'behind' the Contour Plot can be employed to associate rows into like groups using a number of different criteria, including: similarity by sum-of-the-square-of-the-differences, maximum intensity, and channel of maximum intensity. After the grouping operation is performed, the average spectrum of each group can be calculated and displayed. Using this option, all features or pixels belonging to the same group are mapped to one pseudocolor (as set by the interactive Color-Grouping Bar) and the average spectrum of each group is displayed in the Plot Window. In MTID, the vertical axis of the Plot Window corresponds to fluorescence intensity. However, the horizontal axis is more complex, and is comprised of multiple group intensities repeated for each channel. We will use the results of a seven-species MTID experiment (shown in FIG. 7) for further explanation of this unique type of grouping operation and histogram display.

Figure 7:
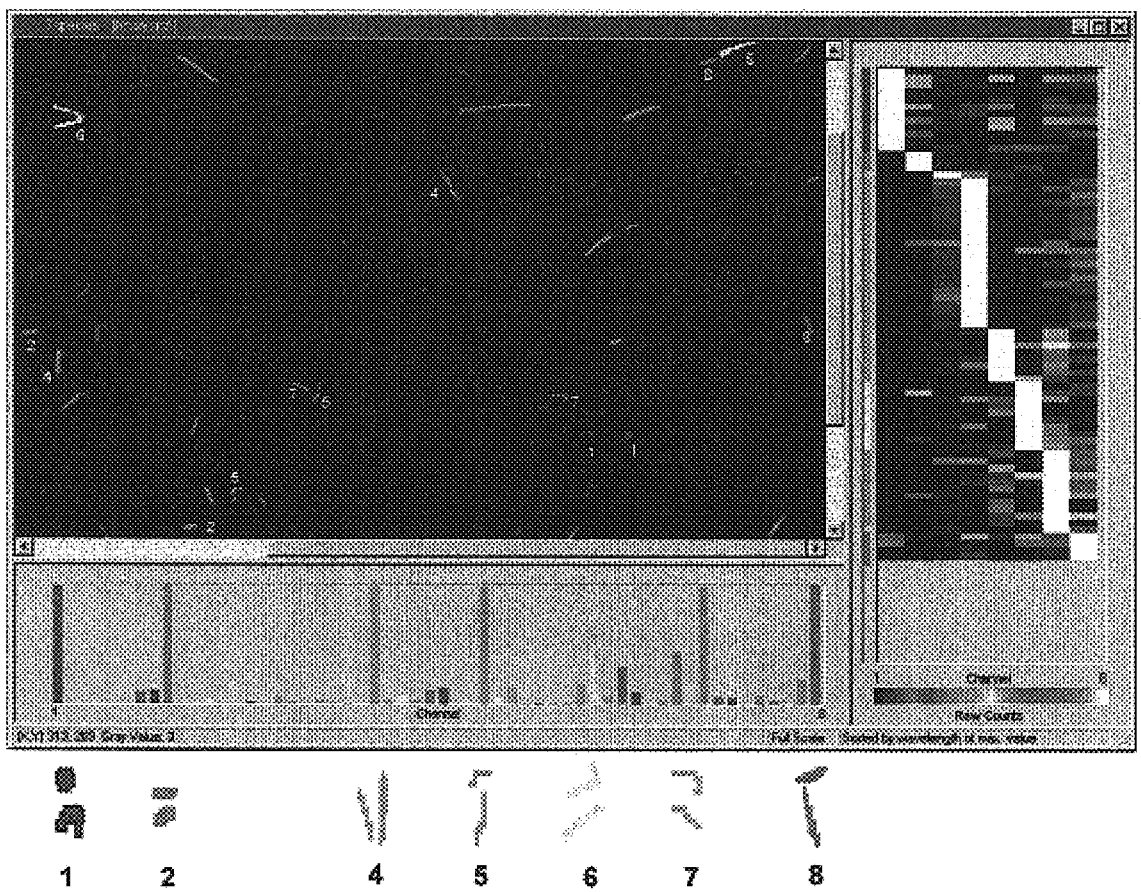
FIG. 7 Graphical user interface for the MTID instrument demonstrating the identification of 7 bacterial species using multispectral detection of fluorescent probes. The MTID instrument measures the fluorescence intensity in all eight channels for every pixel in the image (Channel 3 was reduced to facilitate sorting). These spectra are sorted, grouped, assigned a pseudocolor, and then used to back-paint the image and identify the species that are present. Below the GUI, we have enlarged 2 bacteria from each of the seven groups (against a white background) simply to avoid some color degradation that occurs in the RGB to CMYK printer conversion. Numbers correspond to the probes and species listed in FIG. 18. Channel 3 would normally be used for the universal probe.

FIG. 7 shows a pseudocolored image of the hybridization pattern of eight probes to the seven species that are described in FIG. 18. The Contour Plot has been sorted by the channel of maximum intensity into seven groups. The average spectrum for each group has been calculated, and an assigned pseudocolor is associated with the rows in the Contour Plot by the vertical Color-Grouping Bar. Using these pseudocolors, pixels in the image are back-painted. Starting from the leftmost histogram bar in the Plot Window, the intensity of Group 1 in Channel 1 appears as a full-height purple bar corresponding to the upper-left high intensity region of the Contour Plot, where the fluorophore indicative of Channel 1 shows highest intensity. Groups 2 through 7 show no intensity (black) in Channel 1; hence, no other histogram bars are present except for a short bar associated with Group 8 (encoded in red). Moving further to the right in the Plot Window, we see a total of eight groupings of seven vertical bars for each of the eight Channels—a total of 56 histogram bars. It should be noted that while FIGS. 6 and 7 depict the Plot Window as repeating the series of Groups for each Channel, this information can also be shown as the series of Channels repeated for each Group.

In summary, along with control experiments using single probes (not shown), FIG. 7 demonstrates successful separation of the spectral signals from eight different fluorescent probes, correction for spectral overlap (described below) and back-coloring each different species. The data presented in FIG. 7 also contain information on the universal probe (Channel 3) to normalize the other channels for differences in the number of ribosomes per cell. Finally, it should be noted that the spectra have been automatically sorted using the Contour Plot, and this enabled us to 'backpaint' the bacteria in the image based on their multispectral fingerprint. Thus the MTID instrument can determine whether a particular species is present. Calibration and spectral overlap correction are achieved by methods that will be described in the next section as part of a more detailed description of this aspect of the invention.

Methods for Calibration and Spectral Overlap Correction

Figure 8:
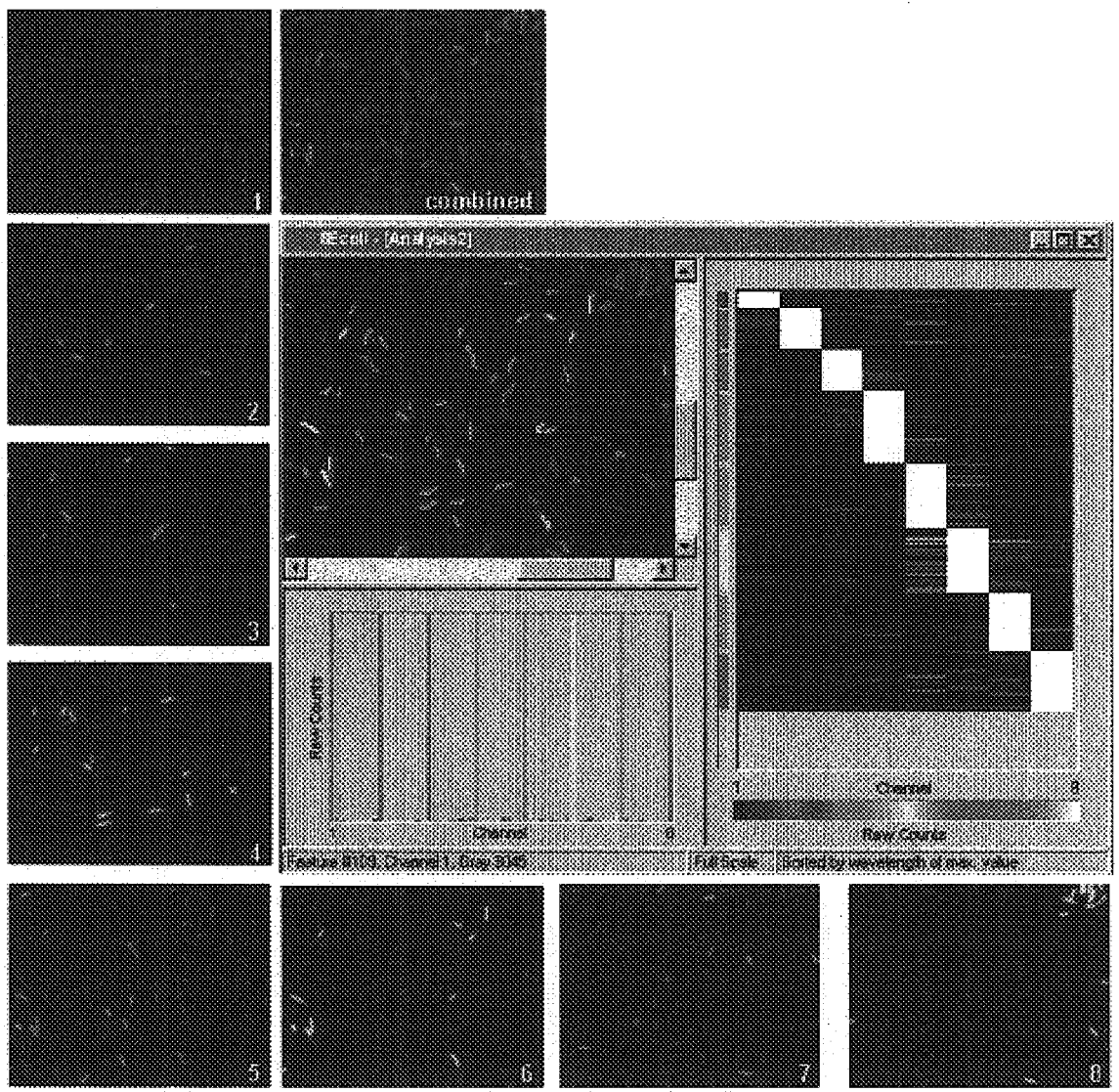
FIG. 8 Graphical user interface for the MTID instrument (center) and the eight grayscale images used to calibrate the probes and filter set described in the text. The combined image is the arithmetic sum of the entire image stack (images 1–8). Data in the Contour and Plot Windows are shown using variable or full scale deflection. A fixed scale display stretches spectral data to the minimum and maximum intensities of the entire dataset.

A method for calibration of all system responses and fluorophore-probe characteristics was developed. Briefly, this method divides the universal probe into eight different aliquots, where each aliquot contains a universal probe labeled with a different one of the fluorophore tags listed in FIG. 18. A culture of *E. coli* bacteria is grown to upper-log phase and divided among these eight different hybridization reactions. The bacterial and probe aliquots are hybridized individually and then deposited on a single "calibration slide". A region-of-interest (ROI) is selected that contains all eight probe types (FIG. 8). Using the following matrix algebra, we were able to obtain calibrated "hybridization units" rather than raw grayscale values; this takes into account the response of the lamp, filters, CCD chip, and the interaction of this particular set of dyes with the selected excitation, dichroic, and emission filters.

The data shown in FIG. 8 comprise a 'calibration standard' of *E. coli* cells that have been hybridized in separate reactions using an identical universal probe tagged individually with eight different fluorophores. This was done to determine the degree to which our spectral-correction algorithms separate the members of a well-defined population. In fact, the calibration data from this experiment were also used in the seven-species experiment (FIG. 7, shown previously). The outer set of monochrome images shown in FIG. 8 comprise an image stack in which residual spectral overlap causes some bacteria to be visible in more than one image. After spectral correction and sorting, the Contour Plot shows a strong diagonal element. In fact, this is the graphics equivalent to the identity matrix [I] described below.

Using MTID spectral export functions, raw data for each of the eight different color-coded groups shown in FIG. 8 was separately exported to construct the 8×8 matrix [G]. Analogous to a contour plot, spectral channels are represented by columns and spectral groups are represented by rows:

$$[G] = \begin{bmatrix} g_{11} & g_{12} & \cdots & g_{1n} \\ g_{21} & g_{22} & \cdots & g_{2n} \\ \vdots & \vdots & \vdots & \vdots \\ g_{m1} & g_{m2} & \cdots & g_{mn} \end{bmatrix} \quad \text{Equation 1}$$

In the special case of a calibration slide, groups differ only in the identity of the fluorophore tag, hence we can consider the columns to be representative of the particular dyes. Using raw data that was processed in order to construct the image shown in FIG. 8, the [G] matrix is equal to that shown in FIG. 20.

For example, $g_{22}$ of Equation 1 represents the average grayscale intensity of dye 2 in Channel 2 (i.e., uncorrected image 2). Element $g_{23}$ of Equation 1 represents the intensity of dye 2 in Channel 3. If spectral overlap did not occur, $g_{23}$ (as well as all other off-diagonal elements) would equal zero. In order to correct for spectral overlap and for instrument response, we can determine a calibration matrix [C] such that $$[C][G]=[I] \quad \text{Equation 2}$$

Here, [I] is the identity matrix with all off diagonal elements equal to zero and diagonal elements equal to unity. It is easy to show that [C] is the inverse of [G], or effectively:

$$[C]=[G] \quad \text{Equation 3}$$

In order for an inverse to exist, the [G] matrix must not be singular. This will be true unless some dyes are actual (spectral) combinations of other dyes. Because such dye combinations are not used in our dye set, matrix [G] is nonsingular and thus we can solve for [C]. An example of a [C] matrix is shown in FIG. 21. In future measurements, matrix [C] can be redetermined for any particular dye set or experimental setup involving a change of optics. Otherwise, it is a constant set of parameters that can be used to achieve calibration to remove spectral overlap among the dyes within a set.

If the matrix [G] is of the general form:

$$[G] = \begin{bmatrix} g_{11} & g_{12} & \cdots & g_{1n} \\ g_{21} & g_{22} & \cdots & g_{2n} \\ \vdots & \vdots & \vdots & \vdots \\ g_{m1} & g_{m2} & \cdots & g_{mn} \end{bmatrix}$$

and m is equal to n, then the matrix can be solved according to Eq. 3. However, if n is less than m, the matrix will be under-determined, if m is greater than n, the matrix is over-determined. For both the under- and over-determined cases, a pseudo-inverse can be found and matrix [C] can be calculated by singular value decomposition (SVD) as shown in "Numerical Recipes in C", by Press et al., published by Cambridge University Press, 1988. The example shown here is for a square matrix where m equals n, but these methods are generally applicable for all values of m and n greater than or equal to 2.

After solving for the calibration matrix [C] using techniques such as the Gauss-Jordan elimination, we can apply this matrix to each pixel within the uncorrected image stack:

$$\begin{bmatrix} c_{11} & c_{12} & \cdots & c_{18} \\ c_{21} & c_{22} & \cdots & c_{28} \\ \vdots & \vdots & \vdots & \vdots \\ c_{81} & c_{82} & \cdots & c_{88} \end{bmatrix} \begin{bmatrix} y_1 \\ y_2 \\ \vdots \\ y_8 \end{bmatrix} = \begin{bmatrix} x_1 \\ x_2 \\ \vdots \\ x_8 \end{bmatrix} \quad \text{Equation 4}$$

Figure 9:
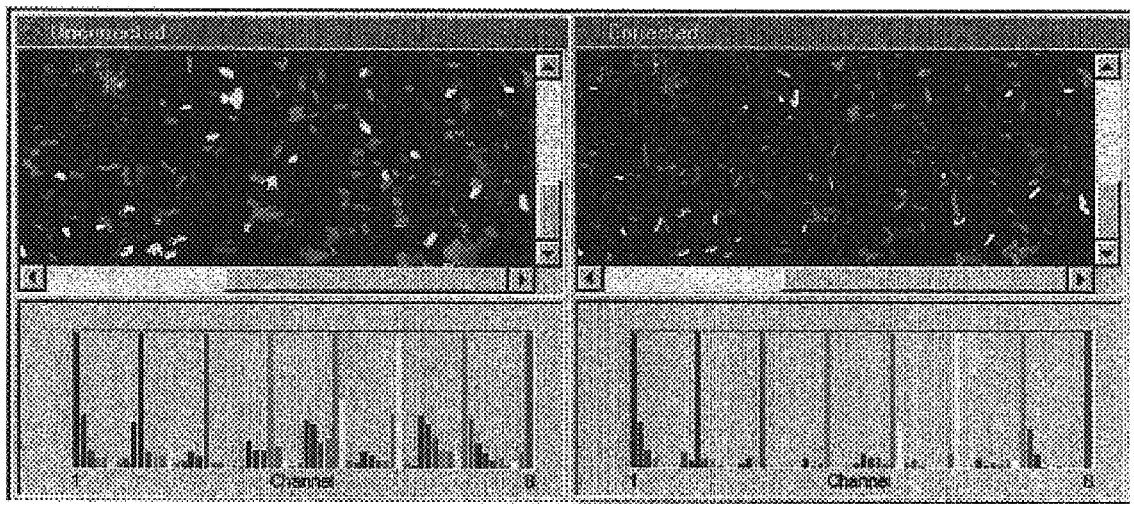
FIG. 9 The MTID Image Windows (top) and Plot Windows (bottom), before (left) and after (right) applying the spectral overlap algorithms described in the text. The corrected Image Window is identical to the fully processed Image Window in FIG. 8, except that a different region of interest (ROI) has been chosen.

The vector [Y] represents the measured (uncorrected) intensity of a pixel in each of the eight images (i.e., channels). The spectral overlap-corrected intensity values of this pixel in the corresponding 8 corrected channels are given by the vector [X]. The effect of this correction has already been pointed out in FIG. 8, which shows a substantially diagonalized contour plot for the special case of using [C] on the sample from which it was derived, i.e., a calibration slide. The effect of the correction on the Plot Window's histogram representation is shown in FIG. 9, where the occurrence of a 'group' outside of its expected channel is minimized. After correction, each spectral group is more prominent in its representative channel. For the end-user, this correction is most apparent in the Image Window, where individual bacteria are back-colored more precisely.

Since rRNA content is known to vary depending on the species and growth conditions, a further normalization may be required in some cases to equalize the signals observed in all channels to a single 'universal' probe. In the seven-species identification experiment presented in FIG. 7, we reserved Channel 3 for a universal probe. The intensity of dye 3 in Channel 3 can be used in this normalization after spectral overlap corrections have been made. Thus Eq. 5 further processes the output of Eq. 4 (in terms of the entire corrected image stack) to generate fully corrected and normalized spectral signatures for MTID:

$$\frac{S}{x_3} \times \begin{bmatrix} x_1 \\ x_2 \\ \vdots \\ x_8 \end{bmatrix} = \begin{bmatrix} n_1 \\ n_2 \\ \vdots \\ n_8 \end{bmatrix} \quad \text{Equation 5}$$

Where vector [N] contains the normalized intensity values. The value $x_3$ is the spectral overlap-corrected intensity value for the universal probe channel, which is (arbitrarily) Channel 3 in this case. S is a scaling constant for all pixels that returns the grayscale values to levels appropriate for 16-bit integers, i.e., the CCD camera's initial dynamic range. For S=1, the [N] vector can be considered to represent "hybridization units" on a scale of zero to one, i.e., ranging from no hybridization of the probe to a level equivalent to the universal probe (unity).

This combination of fluorescent standards and matrix-based overlap corrections has general utility for a wide variety of fluorescence and other spectroscopically-based imaging applications where a set of affinity agents (such as a probes, sensors or other indicator molecules) are used to generate multiplexed spectroscopic signals.

To demonstrate the calibration of MTID achieved with this method, inefficient and time-consuming auxiliary programs outside of the main MTID software program were used to perform the matrix algebra and image processing steps. However, software can be written that automates some or all these steps. As seen by the end-user, all image acquisition and calibration of the instrument can be combined into a single wizard-guided process in the main MTID program by extensively modifying the MFC/C++ computer code.

Biochemical Methods and Sequence analysis for Multispectral Identification

Figure 2:
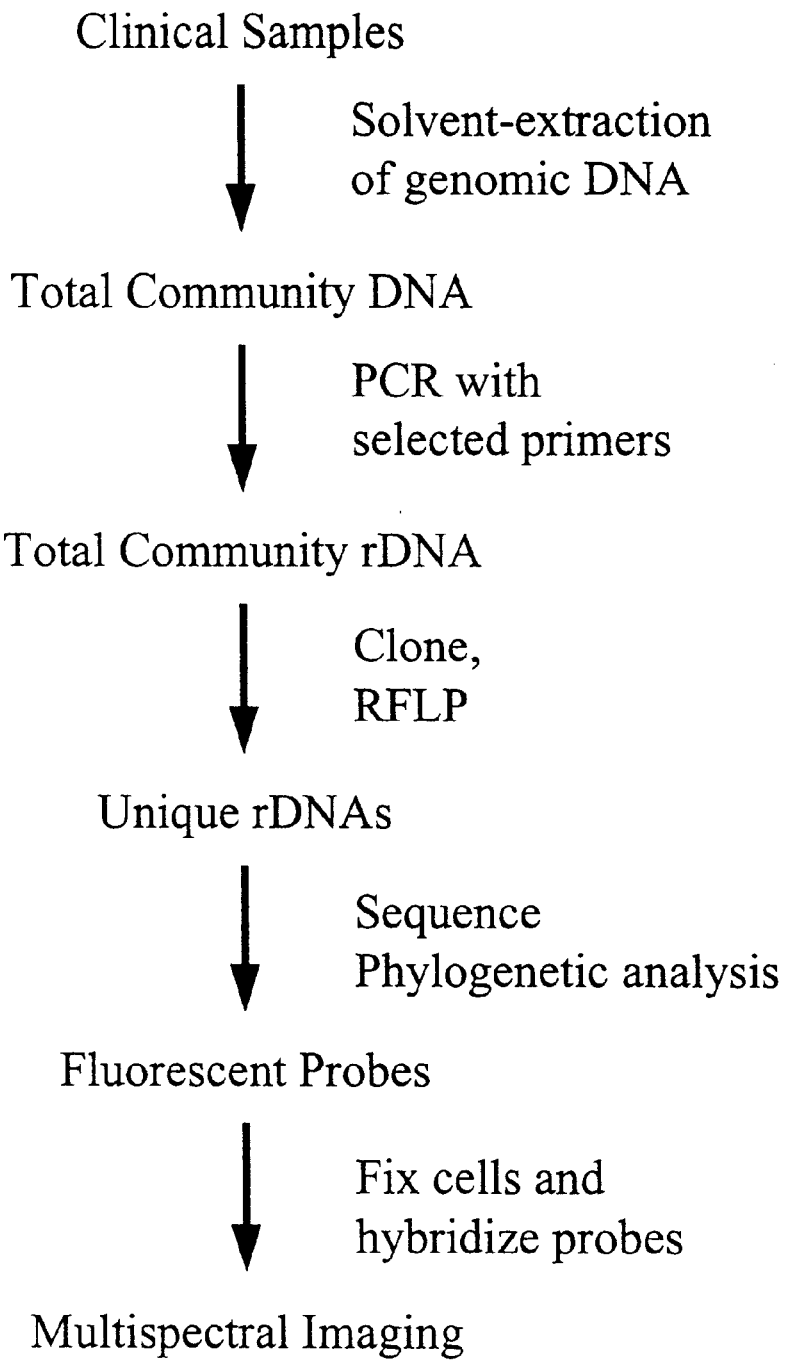
FIG. 2 Flow chart of the steps undertaken to identify microorganisms by molecular techniques. This process eliminates the need for isolating microorganisms in a complex community. Once an rDNA sequence such as the 16S rRNA gene is determined, labeled hybridization probes are designed and tested in situ. Validated probes can then be re-utilized to identify microbes in subsequent samples. In the MTID system, such hybridizations can be multiplexed to simultaneously identify up to seven or more uniquely. labeled probes.

Having completed the development of hardware, spectral correction algorithms, and software needed to perform accurate identification on test samples, we directed our efforts toward identifying bacteria in actual clinical samples. Here, we demonstrate how the MTID system can function as a new tool for medical researchers who need to better analyze the diversity of microbial populations in complex biological specimens. To accomplish this task, a logical progression of steps is performed that employs molecular methods to identify the bacteria (see FIG. 2). Thus, by using procedures that are now standardized, small-subunit (16S-like) rRNA genes are amplified by PCR from samples (fluids or tissues). These genes are then cloned, sequenced, and phylogenetically compared with the rRNA database to identify microorganisms associated with the material. Bacterial sequences that are found to be unique or that appear to be enriched in diseased tissue represent candidate etiologic agents. During the course of these studies, normal fluids or tissues are examined for microbial content, if any, and compared with the diseased sample as a control. Bacterial identification by PCR and sequencing thereby provides unique signatures for the design of 16S rRNA probes. These fluorescent probes are then used to further examine the samples in situ by high-throughput screening. After describing the preparative methods involved (sections a, b, c, below), we will discuss applications of MTID in investigating prostatitis and vaginosis. Finally, we will describe methods for coordinating primer design and probe diagnostics based on the use of MTID at the level of phyla and subdivisions.

(a) Isolation of genomic DNA and PCR amplification. DNA is isolated from disease samples by well-established methods that have been developed for environmental samples. Prostatic fluid is collected in a sterile, screw-capped container. Vaginal specimens are collected using a standard swab transport system. Both sample types are frozen upon receipt by the clinical laboratory and transferred to the MTID facility on dry ice. Samples are subjected to proteinase K and lysozyme digestion, followed by bead-beating (100 μm-diameter zirconia/silica beads) in the presence of SDS, phenol, and chloroform. This procedure is highly efficient in extracting nucleic acids from virtually any cell type, without significant damage to 16S rDNA sequences. After a phenol/chloroform extraction and ethanol precipitation step, the genomic DNA is used for PCR amplification (Weisburg et al., 1991). Genomic DNA is amplified with AmpliTaq Gold (Perkin-Elmer, Norwalk, Conn.), utilizing a variety of PCR protocols to insure complete coverage of all organisms.

A variety of primers can be used to amplify 16S-like rDNA at various taxonomic levels: (1) universal primers that are general for all three domains of life, (2) domain-level primers that select for Bacteria, Archaea, or Eucarya sequence types or (3) more specific primers that select for genera or species (Pace et al., 1986; Olsen et al., 1986; Giovannoni et al., 1988; Barns et al., 1996). Universal primers pose a disadvantage in the case of human tissues, because amplification of host rDNA can overwhelm a clone library. Use of bacterial or group-specific (e.g., Low G+C gram positive-specific) primers minimizes background due to host tissues because human 18S and mitochondrial rDNA do not serve as efficient templates with such primers.

(b) Cloning, RFLP analysis, and sequencing of mixed-species 16S-like rDNA. PCR products can be cloned using the TOPO TA cloning procedure (Invitrogen, Carlsbad, Calif.; Shuman, 1994). This method is advantageous for isolating unknown 16S rDNA sequences because it does not require restriction sites for cloning. Instead, TOPO TA takes advantage of single overhanging adenosine residues that are generated by Taq DNA polymerase during PCR. The PCR product can therefore be ligated directly into a vector that has been linearized with single overhanging thymidine residues.

Individual clones can be prepared by the 96-well DNA mini-prep method of Ng et al. (1996). To identify unique sequences, clones are first sorted by a high-resolution restriction fragment length polymorphism (RFLP) test (see FIG. 10; Hugenholtz et al., 1998a). As information about the types of sequences accumulates, RFLP patterns become diagnostic and extensive sequencing is reduced considerably. Unique clones are sequenced using an automated sequencer.

Although PCR/RFLP analysis is extremely powerful, it is not without some problems, which must be controlled. For example, community analysis by PCR is fraught with potential artifacts such as "chimeric" clones. Chimeric clones result from the recombination of different rRNA genes during PCR of mixed species rDNA. Chimeric sequences present a problem in the sequence analysis, since amplification of chimeric sequences will cause one to overestimate the biodiversity of a diseased sample. It will also generate incorrect rRNA sequences. Chimeric sequences can be detected by: (1) a separate phylogenetic analysis of the 5' and 3' halves of each rRNA sequence, (2) a search for discrepancies in long-range secondary and tertiary interactions in the well-established phylogenetic structure of 16S rRNA, and (3) a test available from the Ribosomal Database Project, the CHECK_CHIMERA program (Maidak et al., 1997). This program searches for any part of the sequence that deviates from that of its closest relatives using a set of reference sequences. Increasing the extension time during PCR may help to reduce the chance that rDNA fragments will generate chimeric sequences.

Contamination of samples with foreign organisms is another potential problem. Exogenous DNA or the DNA present in various organisms can contaminate reagents, including enzyme preparations (Tanner et al., 1998). To control for this possibility, a sample is prepared without added tissue but with the addition of the same solutions used in the isolation of genomic DNA.

(c) Computer Alignments and Phylogenetic Trees. Sequences obtained through PCR are first processed in the Sequence Navigator application (Applied Biosystems) and then compared with the GenBank database using a BLAST Search (NCBI; Altschul et al., 1997). The BLAST search is useful for screening sequences with close matches to those in GenBank. To determine phylogenetic trees, a number of methods based on different principles and assumptions are commonly used (Maidak et al., 1997; Fink, 1986). GDE (genetic data environment) is an interactive sequence editor capable of running phylogenetic tree building programs. The PHYLIP program (Felsenstein, 1989) (PHYLogeny Inference Package) integrated into GDE, allows for parsimony, distance matrix, and likelihood methods. Resampling methods, such as the bootstrap and jackknife, can also be used to evaluate the statistical significance of the phylogenetic trees (Felsenstein, 1988).

A variety of computer programs are available for phylogenetic analyses of the large and small subunit rRNA sequences. The most comprehensive software is the ARB program ('arbor', Latin for tree). Designed by Strunk, Ludwig, and colleagues at the Technical University of Munich (Strunk et al., 1996), ARB integrates sequence alignment and treeing programs for phylogenetic analyses.

The following examples are intended to illustrate but not to limit the invention. While they are typical of those that might be used, other procedures known to those skilled in the art may alternatively be used.

EXAMPLE 1

Analysis of Prostatitis as a Model System

This example shows the feasibility of the method of the invention in analyzing complex clinical samples that may contain previously unknown organisms. In a prostatitis study now in press (Tanner et al., 1999), corynebacteria and other genera were identified by PCR and sequencing of 16S rRNA genes. Many of these species may be very difficult to culture, but they are potentially important in the etiology of the disease. Some of these corynebacteria are not closely related to known species and may represent hitherto uncharacterized species. Multispectral probing of the 16S rRNA gene is advantageous because the method does not rely on the cultivation of bacteria and can identify species more accurately than cultivation alone.

Figure 11:
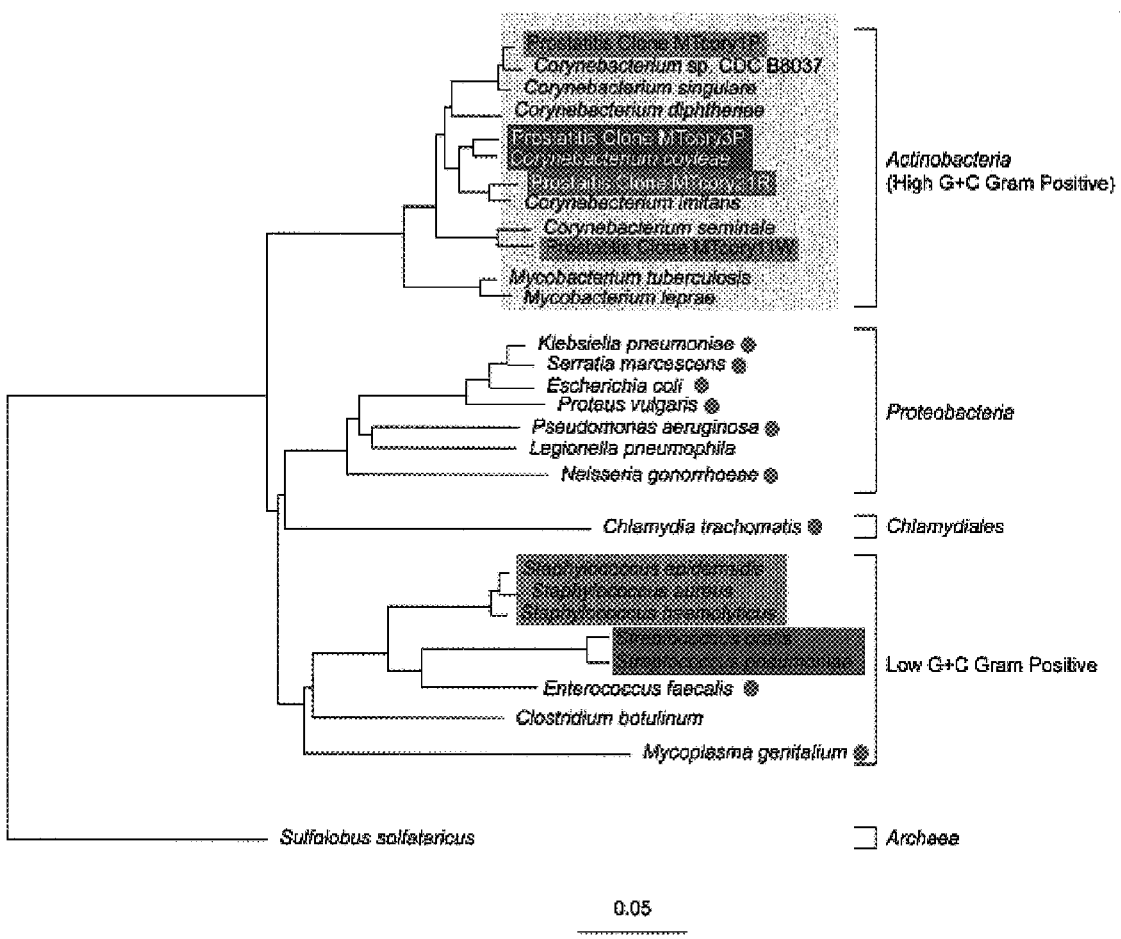
FIG. 11 Phylogenetic tree of selected bacterial species identified in expressed prostatic secretions from prostatitis patients. The color-coding scheme shown in FIG. 22 identifies the species that will hybridize to species-specific, genus-specific, or universal probes. The probes for Channel 1 will hybridize to both *Corynebacterium coyleae* and Prostatitis Clone MTcory3P. Species commonly cited as uropathogens which have a potential for causing prostatitis are indicated by red dots. With the exception of *E. coli*, these common uropathogens were not found in the published prostatitis study. The tree was rooted with the archaeal species *Sulfolobus solfataricus*.

Prostatitis samples can be examined with a multispectral set of probes that are targeted to these newly described corynebacterial 16S rRNA genes. A set of seven probes can be designed to target specific species of corynebacteria, as well as the genera Staphylococcus and Streptococcus, which may also be associated with prostatitis. A second probe set can be made to target other genera prevalent in prostatitis (i.e., Peptostreptococcus sp., Gemella sp., *Propionibacterium acnes*, and *Escherichia coli*). The second set includes a mixture of species- and genus-specific probes. FIG. 22 lists probes, hybridization sites on the 16S rRNA, fluorescent labels, and target organisms. FIG. 11 shows the evolutionary positions of these bacterial species relative to other common pathogenic bacteria.

Expressed prostatic secretions (EPS) can be obtained through a clinical laboratory. EPS contains proteins, sugars, trace elements, and prostaglandins, but usually not sperm. In preparation for MTID analyses, EPS samples are centrifuged to pellet bacteria and are then resuspended in sodium phosphate buffer. This is followed by two wash steps to ensure the bacteria are suspended in sodium phosphate buffer that is free of significant contaminants from the EPS. The cells are fixed by incubation in 4% paraformaldehyde for three hours at room temperature. Our earlier experiments showed that hybridization in suspension can be performed successfully on ATCC-derived bacterial species. This procedure can also be used for prostatitis samples. The detergent NP-40 is added to the cell suspension at a final concentration of 0.1%, and the cells are centrifuged. The pellet is then passed through a series of dehydration steps by resuspending it in 50%, 80%, and 100% ethanol, respectively. After drying, the cells are resuspended in the hybridization buffer, prehybridized for 30 min at the desired temperature, and then hybridized 12 to 24 hours with the probe ensemble. The cells are again centrifuged and washed to remove nonspecific binding probes. Cells are then resuspended in a final buffer, and a small volume is loaded onto slides for microscopy. In addition to performing MTID on positive prostatitis samples, analysis must also be performed on control (non-prostatitis) EPS. The species of bacteria that have been identified can be compared with those found in samples from other patients. The effect of various therapies or other clinical variables on the species composition of the EPS can also be compared in order to better understand the etiology and development of the disease, to improve diagnosis and testing, and to direct appropriate treatment.

EXAMPLE 2

Analysis of Bacterial Vaginosis as a Model System

In this example, the MTID system is used to study how the distribution of various species in a complex bacterial population changes over time, potentially in response to various treatments. Numerous diseases that may result from changes in bacterial consortia (i.e., complex interacting populations of species), such as otitis media, tonsillitis, and bacterial vaginosis could benefit from this type of analysis. Bacterial vaginosis is the most common cause of vaginal discharge and is the most common vaginal infection among women of reproductive age (Gardner & Dukes, 1955; Amsel et al., 1983). As a public health problem, it accounts for millions of office visits per year in the United States (Sparks, 1991). It also has been linked to increased risk of pelvic inflammatory disease, postcesarean delivery endomyometritis, posthysterectomy pelvic infection, chorioamnionitis, premature rupture of membranes, and preterm labor and delivery (reviewed in Eschenbach, 1993).

The etiology of bacterial vaginosis has not been precisely determined, although numerous factors maybe involved (Priestley & Kinghorn, 1996). The most notable bacteriological correlation with the disorder involves a shift in the population distribution of the vaginal flora. In healthy women, the vaginal ecology is dominated by Lactobacillus species. These bacteria produce lactic acid, which lowers the ambient pH, as well as $H_2O_2$, which is lethal to catalase-negative bacteria such as Gardnerella, streptococci, and anaerobes. Under normal conditions, the lactobacilli thus inhibit the growth of other commensal microorganisms, such as *Gardnerella vaginalis*, with which the lactobacilli are capable of forming a biofilm in laboratory culture (Muli & Struthers, 1998). In the pathogenic state, a cocktail of various bacteria is present. In addition to Gardnerella, this has been shown to include Prevotella and Mobiluncus species, as well as Fusobacterium, Bacteroides, and Peptostreptococcus (Hillier et al., 1993). Mycoplasma species are also sometimes found. At the same time, the concentration of Lactobacillus is greatly reduced. The factors that cause the shift to abnormal flora are not understood, and it is also not known how much some of the minor species contribute, if at all, to the pathology.

The ability to characterize complex microbial populations, especially those that contain species that are difficult or impossible to cultivate, is of critical interest to the medical microbiology research community. A more efficient system for analyzing these populations will greatly assist efforts to understand the origin and dynamics of these diseases. The study of vaginosis is a particularly good example of how MTID technology can be applied. Although basic clinical test kits, such as the Becton-Dickinson Affirm VPIII system, are commercially available for diagnostic use, they do not fully address the needs of researchers for sophisticated microbial analysis.

Figure 12:
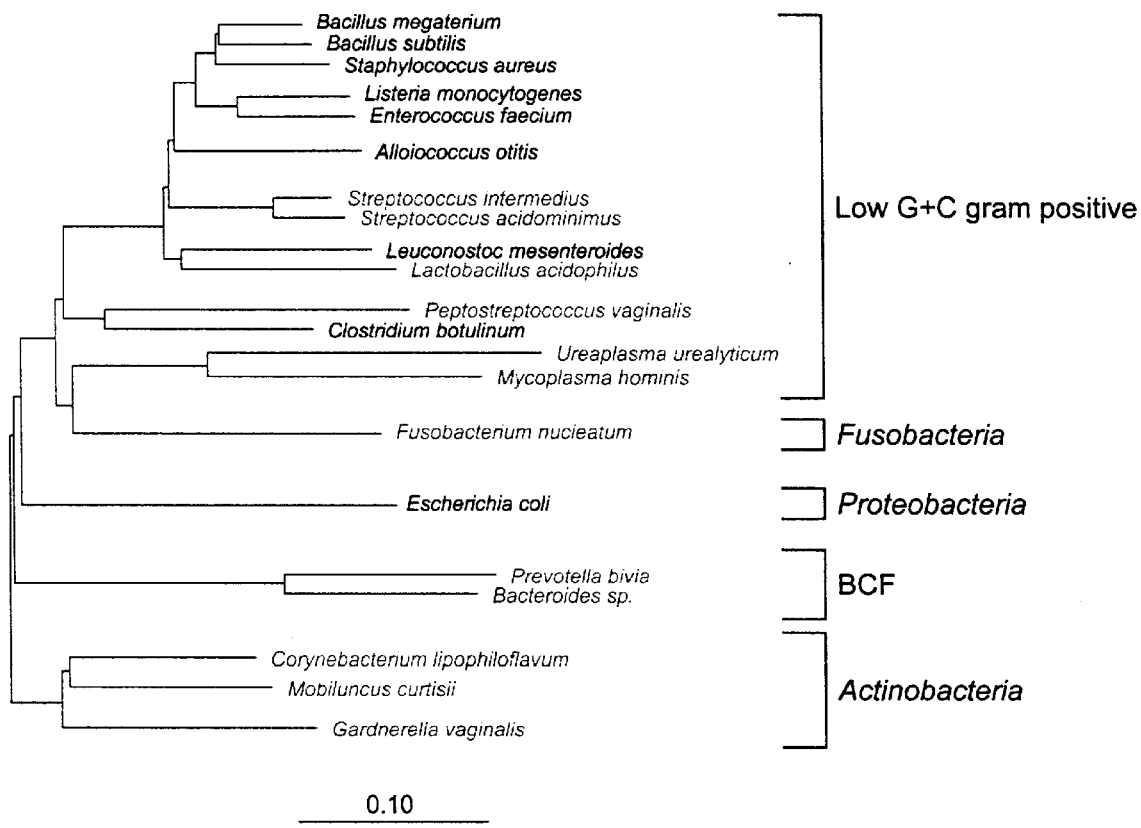
FIG. 12 Organisms associated with vaginosis (lighter text) grouped into their respective phyla. Additional organisms were included for reference only. The tree was rooted with the archaeal species *Sulfolobus solfataricus* (not shown).

Studies of the effect of various antibiotics on the microbial flora will also benefit from a more accurate and quantitative assessment of the bacterial populations. This could include, for example, tracking the microbial population diversity over time from a number of patients. This will assist researchers in understanding the fundamental causes of the disorder, including the continuum of events leading to a change in the microflora. Organisms currently thought to be involved in vaginosis can be grouped into four separate phyla within the Bacteria (FIG. 12).

Samples for MTID analysis of bacterial vaginosis can be obtained through a clinical laboratory. There are two strategies that can be used to study these samples. The first, based on published knowledge of the species involved, uses four phylum-specific probes to quickly obtain general information about the genetic diversity of the disease versus the control samples with in situ imaging. For more detailed information, and to check for any previously unrecognized, species, DNA from the samples can also be prepared using a procedure similar to that described above for the prostatitis samples. After PCR amplification of the 16S genes and cloning into vectors (using the methods described in Tanner et al., 1999), RFLP analysis is performed to determine the number of different species present. Unique clones are then sequenced. Based on comparisons with known sequences and phylogenetic analysis described above, a set of probes is designed to identify particular species in situ. Procedures related to RFLP analysis, sequencing and species-specific probe design are identical to the prostatitis analysis described in example 1, above.

EXAMPLE 3

Selective Identification of Potential Pathogens

Some studies in analytical microbiology would benefit from relatively selective identification of species. It might be advantageous, for example, to be able to identify only potential pathogens in a highly complex clinical or environmental sample. Current methods and instrumentation, however, cannot cover such a wide range of species simultaneously. The advantage of the MTID system is that it can simultaneously analyze eight probe sets. Moreover, these probe sets can be specifically designed to highlight particular taxonomic groups, so that the analysis is considerably more focussed. In this example, we show how a probe set can be designed to identify members of bacterial divisions that are known to contain pathogenic species. There are now approximately 40 phyla of Bacteria, with about 13 known exclusively from molecular phylogenetic analyses of their 16S rRNA. Remarkably, only seven of the phyla are known to have pathogenic organisms. These are highlighted in FIG. 13. Since the population dynamics of bacteria may be very important in the progression of disease, we have designed probes to all seven of these bacterial phyla for simultaneous identification. This single probe set can identify all the known phyla that contain pathogenic members and will be valuable for determining the overall diversity of a given clinical sample.

Figure 13:
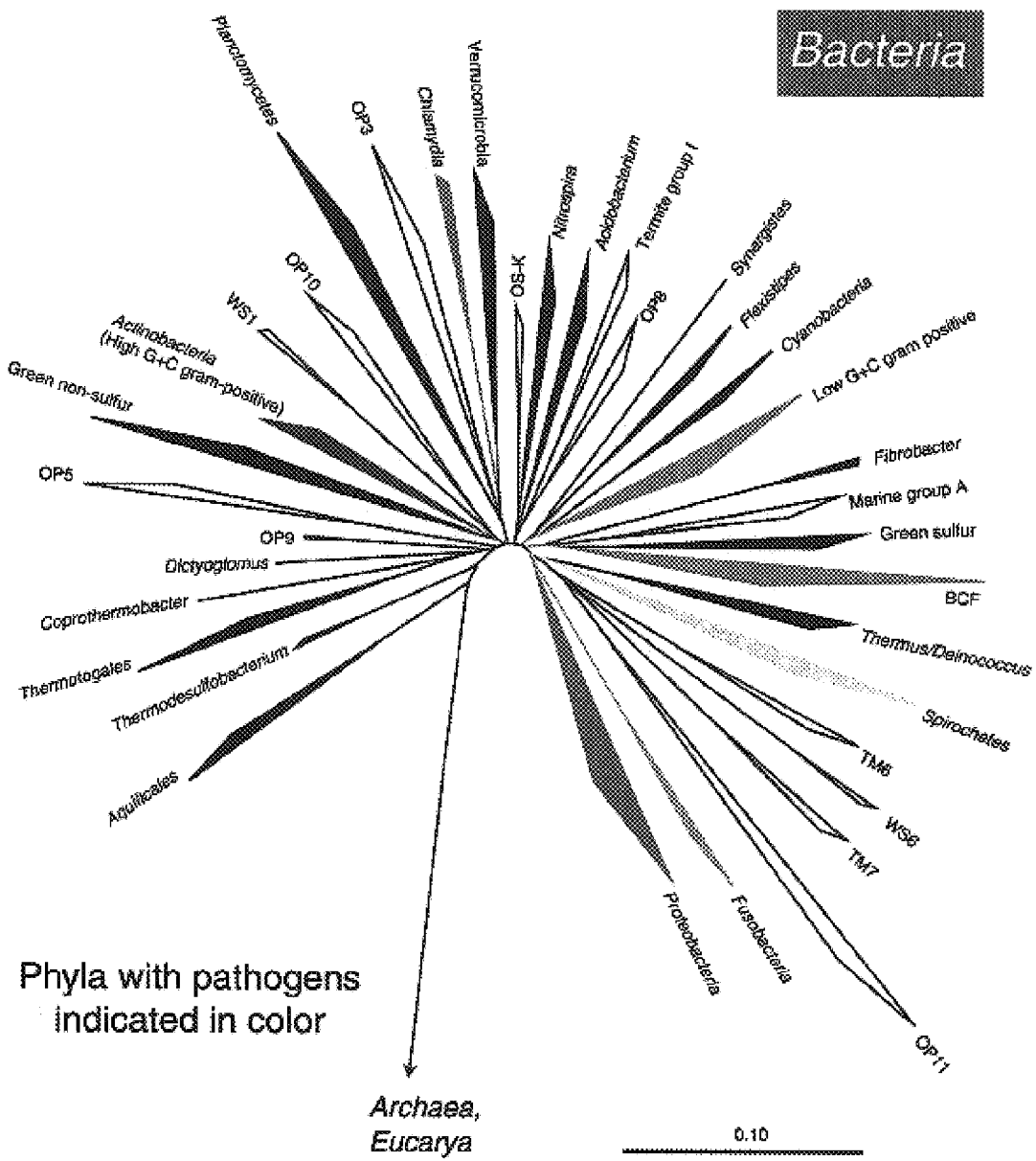
FIG. 13 Bacterial phyla known to contain pathogenic species. Pathogens have been identified in at least seven different phyla (shown in color). Adapted from Hugenholtz, et al., 1998b. Unfilled wedges represent phyla with no cultured members.

It is clear from FIG. 13 that a set of seven phylum-specific probes could be useful for initially surveying complex populations of pathogens. In fact, in the case of bacterial vaginosis, one might expect to see immediate differences at the phylum level between disease and normal samples. For example, a population shift from Lactobacillus to Gardnerella is expected to be apparent at the level of phyla as a decrease in the ratio of probes hybridizing to (Low G+C) gram positive bacteria versus Actinobacteria. This approach can be expanded to follow the dynamics of all seven of the phyla that contain pathogenic species using the probes shown in FIG. 23. In such experiments, it is important to include a universal probe to indicate whether the sample contains a previously unknown pathogen from a different phylum. It is also important to enhance probe-design software to cover all of the genera within the known, pathogen-containing phyla to a high degree of completeness. With existing software, three or four probe sequences were required to get near complete coverage of the phyla with large numbers of species (i.e., the Proteobacteria, Actinobacteria, and Low G+C gram positive). FIG. 23. Fluorescent oligonucleotide probes directed against the 16S rRNA of seven bacterial phyla that are known to contain pathogenic species.

The identification of unknown cells by hybridization to rRNA is not limited to bacteria and archaea. Eucarya such as ascomycetes, algae, protists and other cells can be identified by amplifying their 16S-like rRNA, sequencing the RNA genes, designing probes based on the sequences, and hybridizing the probes to the cells (Medlin et al., 1988; Lim et al., 1993). Mammalian cell 18S-28S rRNA can also be probed with fluorescent oligonucleotides (Labidi et al., 1990), and fluorescent probes to the 16S rRNA of human mitochondria have been hybridized in situ to skeletal muscle tissue to identify cells with mitochondrial disorders (Hilton et al., 1994).

EXAMPLE 4

Bioprospecting and Biodiversity Screening

Figure 14:
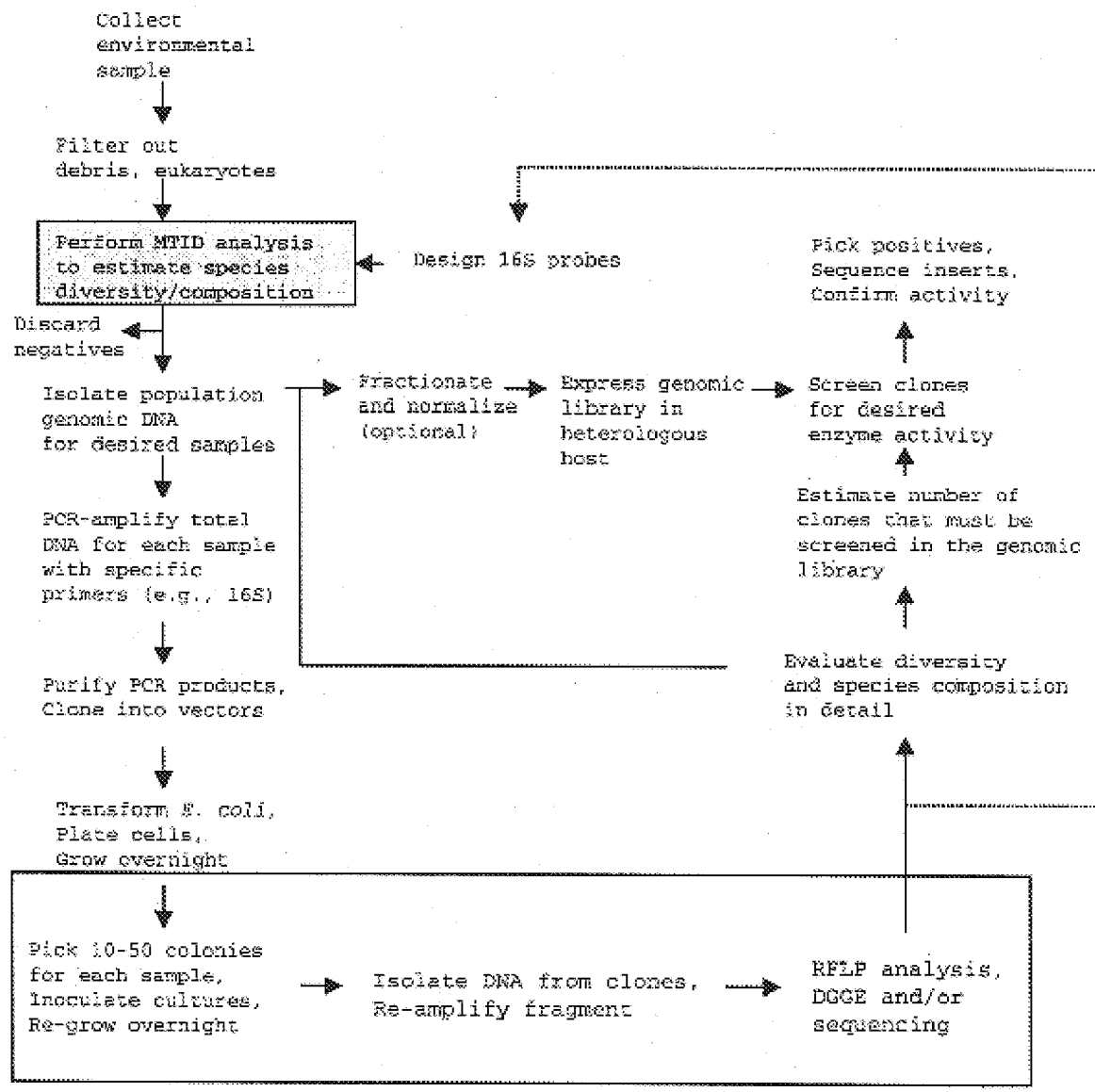
FIG. 14 Flow chart for using MTID for bioprospecting and genomic cloning.

An advantage of the MTID system is that it not only identifies the different taxonomic groups present in a sample, but it also provides information about their absolute and relative abundance. This can be used advantageously in high-throughput screening of environmental isolates (e.g., air, water, soil, and plant material). In this example, MTID technology is applied to bioprospecting for microorganisms that possess commercially useful enzymatic activities, metabolic pathways and bioactive compounds. Similar procedures could also be used for monitoring bioremediation and for assaying mixed-culture fermentation, fluidized bed reactors, or other complex bioprocesses. Environmental biodiversity screening for novel species of bacteria and archaea, as well as simple eukaryotes, has provided a wealth of enzymes for molecular biology, pharmaceutical synthesis and various industrial applications. These include aminotransferases, phosphatases, glycosidases, cellulases, esterases and lipases. Libraries of new organisms from environmental isolates have become a key source of diversity for the industrial enzyme business, and the continued search has been driven by the realization that >99.9% of the bacteria and archaea in the environment have not been cultured. This lack of culturability means that very few of the existing species (only about 5,000) have been classified or characterized (Short, 1997). Thus, there are likely to be large numbers of enzymes with useful activities in the remaining uncharacterized species, which may number in the range of $10^6$ to $10^8$. Current research is also attempting to discover how microorganisms in the environment communicate with each other in order to form highly complex communities, such as microbial mats and other biofilms. Analysis by MTID can be used to study this process and to determine how specialized molecules secreted by some organisms contribute to community development through quorum sensing, chemotaxis, or bacteriocidal activity. At the present time, environmental samples of unculturable microorganisms are usually screened by PCR to determine their overall genetic diversity. The procedure is outlined in FIG. 14. Environmental genomic DNA is isolated by lysing and extracting the sample as described in Section 4, and this pooled DNA is amplified en masse using specific primer pairs. Usually the 16S RNA gene is used as a target because of the high degree of conservation on its 5' and 3' ends and because a large database of 16S sequences is available for comparison. However, this same procedure can also be used for other ribosomal RNA sequences, such as 5S, 23S, and 18S. Occasionally, the gene encoding a particular enzyme can be amplified directly. The PCR products are then 'shotgun' cloned into plasmid vectors and transformed into E. coli. The E. coli are plated out and grown up to generate colonies. Colonies are picked from the plate of transformants, and these clones are grown up individually. Mini-preps are then performed on the various clones. The desired gene fragment is then amplified again by PCR. At this stage, several different methods can be used to assay the diversity of microbial populations. Direct sequencing of the PCR-amplified 16S gene yields the most information for typing and dendrogram construction, but is also the most time consuming. Commercial kits for this procedure, such as the MicroSeq 16S rRNA Gene Kit, are sold through Perkin-Elmer Biosystems (Foster City, Calif.). Denaturing gradient gel electrophoresis (DGGE), which uses differences in mobility to detect DNA polymorphisms, has been widely used in human mutational analysis, and is now being widely employed to analyze microbial communities (Muyzer & Smalla, 1998; Nübel et al., 1999). DGGE systems are available through a variety of vendors. Restriction fragment length polymorphisms (RFLPs), which are described in detail in the previous sections, use restriction digests on the PCR-amplified products to generate unique banding patterns on agarose gels. A commercial device to automate the RFLP analysis of 16S RNA genes (sold as the RiboPrinter) is now being offered by Qualicon, Inc. (Wilmington, Del.). However, this system is designed for clonal isolates of culturable bacteria and has a relatively modest throughput of 200 lanes per week.

Data from these electrophoresis-based analytical procedures is used to determine how many different clones are represented in the sample, and this information is used to make a crude statistical estimate of the species diversity in the original isolate. If the original PCR product is the desired enzyme gene, then the DNA fragment can be directly sequenced and eventually cloned into an expression system. If the PCR fragment is useable only for diversity screening (as in the case of a 16S rRNA gene), then one must go back to the original pool of genomic DNA and shotgun clone this DNA into an expression library for further analysis. This library can be screened for a particular enzyme activity, such as esterase or glycosidase. Positive clones can then be sequenced and further characterized.

Using PCR analysis alone to assess the genetic diversity of environmental samples is not without some difficulties. First, the presence of large numbers of 'weed' species may obscure the presence of other rare but valuable species. It may therefore require a large number of PCR reactions, purifications, and gels to actually visualize the rare members of the population. Second, due to the potentially biased nature of PCR, some species may be over-represented in the amplification products, giving a skewed impression of the population diversity. Third, organic material in the original isolate (particularly humic acid) can interfere with the PCR enzymes, generating false negatives. Although cesium chloride gradient centrifugation or column chromatography can remove these contaminants, these procedures add extra time, labor and expense to the process of screening very large numbers of samples. If most of the isolates turn out to have undesirable species, then this means that a considerable part of the screening effort may have been wasted. Given that the subsequent process of gene library construction and screening (which is based on the PCR results) is even more laborious, it is crucial to have a system that can quickly and accurately estimate the diversity of each isolate at an early stage in the discovery sequence. Even for samples that might not suffer from any of these problems, there is still the severe limitation of low throughput. As illustrated by the number of steps in FIG. 14, the time required to extract, amplify and electrophorese the genes is considerable. Although a Ribo-Printer instrument is useful for handling the later stages of RFLP analysis, the initial stages are still labor-intensive. This is currently a critical limitation to large-scale screening of environmental isolates. For example, if one wished to screen 10,000 different environmental isolates from a variety of sources, it would require analysis of approximately 50 PCR inserts per sample to get a reasonable measure of the diversity in each sample. This means that 500,000 RFLP lanes (or the equivalent) would be needed. Current technology cannot handle this type of load economically.

The MTID system maximizes the efficiency of bioprospecting for enzymes by creating a high-throughput diversity-screening system based on rRNA hybridization, which can be introduced as the first stage in the discovery process. Optical screening with fluorescent probes permits massively parallel analysis of each sample before RFLPs or other analyses are run. At the preliminary level of screening, three of the eight probe channels can be dedicated to determining the domain-level identity of each organism. Thus, one of the probe channels can be dedicated to a bacteria-specific probe, a second to an archaea-specific probe, and a third to a eucarya-specific probe. This makes it possible to count the total number of cells and normalize the signals for ribosome density, as well as to immediately identify the proportion of large-genome eukaryotic 'contaminants' in the sample. The remaining five channels are devoted to probes utilizing adaptable strategies, depending on the suspected level of biodiversity in the sample and the kind of information desired. For example, if the sample is taken from a relatively extreme environment where most of the species are likely to come from one or a few divisions, species-or genus-specific probes can be used. If, however, the sample is likely to be highly diverse, or if the types of organisms are completely unknown, then division-level probes are more appropriate. Separate aliquots of a given sample can also be probed in greater detail, if necessary. An added benefit of the MTID system is that the results displayed in the contour plot can also be displayed as a pseudo-phylogenetic tree of all the taxa in the sample by comparing the data to a phylogenetic database. This enables the user to quickly visualize the overall phylogenetic composition of a sample and decide how best to further process it. Samples with promising diversity distributions are then be passed on to PCR, RFLP analysis (if confirmation of the diversity is needed), sequencing, and genomic cloning.

Diversity analysis is significantly accelerated using this system because many of the treatments and measurements can be performed on whole populations in situ and in parallel. The hybridizations and washes, for example, can be performed on all the samples simultaneously in a microplate format. After these are transferred to a slide (or other optical surface) for analysis, spectral measurements can also be performed in parallel. The ability to defer PCR/restriction enzyme reactions, column purifications and gels to a later stage in the discovery process saves both time and money while increasing throughput. We estimate that a single fully automated instrument can process ~5,000 environmental samples per day while also providing an accurate picture of the microbial diversity. If this system is able to reduce the number of candidate samples for PCR and RFLP or other analysis from 5,000 to perhaps 20, this will generate both significant savings and improved efficiency.

In addition, a more comprehensive measurement of the species diversity is highly beneficial to the later process of genomic cloning. Genomic cloning will benefit by improved efficiency. This is because in order to be certain that a given gene will be retrieved from a genomic library, it is necessary to oversample the library. It is sometimes possible to fractionate the DNA pool (based on G+C content, for example) and thereby normalize the DNA pool to remove 'weeds'. Nevertheless, if a highly desirable gene is known to be extremely rare in the population, then the size of the screen must be increased accordingly. However, one does not want to screen more than is necessary. With better information on the species diversity within a given sample, the size of the genomic screen can be optimized.

As more and more rRNA sequences are recovered via PCR, we will add them to our database of useful sequences (and phylogenetic trees). We will also expand our library of novel hybridization probes based on this new information. Ultimately, we anticipate that genomic expression libraries containing potentially novel enzymes will be screened by KAIROS' MCI/Kcat technology to yield new variants as described in U.S. Pat. No. 5,914,245. The key to rapid screening of the environmental isolates is to use the MTID spectral sorting routines and contour plot to create an informative fingerprint that succinctly conveys the taxonomic diversity of each sample and the number of members of each taxon.

There are also other advantages to having a rapid initial assessment of diversity. Since it is possible to fractionate the environmental genomic DNA (by its G+C content, for example), it will become increasingly important in the future to use diversity information to decide on an appropriate fractionation strategy. Fractionation helps to separate desirable from undesirable genomic DNA in cases where particular species or groups of species are sought. It can also be used to remove a fraction of undesirable DNA that dominates the population. This is particularly important if that DNA is from a large eukaryotic genome. By performing such 'normalization' prior to library construction, it is possible to maximize the extraction of useful genes from complex libraries. Fast screening by rRNA hybridization can be used to develop improved fractionation procedures, which in turn saves time in the genomic library construction and expression steps. Without such improvements, the pool of genomic DNA would need to be significantly oversampled each time, so that rare positive clones are not lost. This requires an increased library size and thus more screening time.

EXAMPLE 5

Employing Phylogenetic Probe Sets as a Screening Strategy

When the sequence of the target organism is already known, a given probe set will produce a unique and reproducible spectrum that can be used to identify the organism. Successful identification of a large number of unknown organisms, however, requires sets of probes that have varying degrees of phylogenetic resolution. In this example, the MTID system is used to tentatively identify completely unknown organisms whose RNA genes may not have been sequenced. One method to accomplish this is to use a 'triangulation' approach that exploits residual levels of cross-hybridization due to sequence similarity. By using the MTID instrument to carefully measure the signal intensity of each probe relative to the intensity previously measured for a known set of organisms, one can 'triangulate' the approximate position of the unknown organism in the phylogenetic tree. This additional dimension of information can be exploited if each probe is designed so that its $T_m$ is inversely related to its phylogenetic distance from a known 'benchmark' organism. If the 'benchmark' probes cover a desired area of the phylogenetic tree, then the location of the unknown organism can be interpolated within this space. Creating this phylogenetic fingerprint is a more challenging engineering task than that of simple fingerprinting.

This strategy requires an increase in probe complexity, and it is therefore more convenient to quantitate the 'level' of hybridization by using the concept of 'hybridization units'. In this more complex scheme for MTID, normalization of a channel becomes increasingly important because the intensity of the emission from a given fluorophore or tag must be quantitated more accurately than in the case of a simple "on-off" (i.e., 1–0) paradigm. We can define a maximum probe 'complexity' (C) as the number of different spectral fingerprints that can ultimately be separated:

$$C = L^D - 1 \qquad \text{Equation 6}$$

Where L is the number of discrete levels of fluorescence intensity that are discernible, and D is the number of different fluorescent dyes. All of the work described above has used a two-level "on-off" strategy, where we could potentially obtain a "fingerprint" with no more than ~$2^7$=128 states. Yet it is clear that simple discrimination of four levels yields: ~$4^7$=$2^{14}$=16,384 states. It is also possible that the complexity of the probe set can be increased by using a larger repertoire of dyes. Possibilities include using narrow bandwidth quantum dots (at cryogenic temperatures) or, alternatively, expanding the spectral range by employing fluorophores that emit in the near infrared. Quantum dots or nanocrystals for bioconjugation are described in Chan & Nie (1998). Exercising the former option simply requires synthesizing quantum nanocrystals with the requisite DNA-probe linkage chemistry, while the latter option requires a CVIF with a 400–1000 nm range. However, this type of approach is appealing because even a very conservative estimate using simple "on-off" quantization and four new dyes yields:

~$2^{11}$=2,048 unique states.

In the simplest embodiment of the fluorescence fingerprint, each spectral channel corresponds to a specific domain within the primary structure of the rRNA. Having engineered a set of 8 probes with approximately the same $T_m$, the signal strength of any channel is related to sequence similarity with the target. Because of variability in the amount of target rRNA, dye quantum efficiency, and the spectral response of the instrument, it is useful include a universal probe and to reserve its channel (i.e. #8) for normalization purposes. After spectral overlap corrections for all dyes and spectral normalization using for example, channel #8, distinct 7-channel data can be displayed and manipulated in the 'DIS' view. In previous FIGS. (6, 7 and 8) data was displayed using a format that shows 'group' distributions for each channel. Displaying the spectral "fingerprint" of a selected bacterium or group of bacteria requires only the simple operation of reformatting the histogram to display channel spectra as a function of group.

By employing the appropriate mathematical transformations, certain aspects of the 'DIS' contour plot can be related to phylogenetic distances, and thus the spectral fingerprint of an unknown organism can be placed within an already fingerprinted phylogeny. For example, if a contour plot contained channel spectra of known organisms, a spectral mining technique could be used to place an unknown spectrum in the phylogenetic tree and determine its relation to the benchmark organisms using a single pass of the DIS similarity sort. This is done by comparing the spectrum of the unknown with each of the other spectra and calculating the sum of the square of differences (SSD) using an equation similar to Eq. 8. The SSD values are sorted by magnitude and can be displayed in the contour plot. Smaller SSD values indicate like spectra and higher sequence homology. In a similar fashion, one could use spectra from a known organism as the reference in order to 'fish' out similar spectra to it from the contour plot. In this scenario, reference spectra could be stored in a library or imported from other DIS analyses.

Multiple single pass SSD sorts could be applied to the data and displayed. With each iteration, one could lock out or exclude spectra from the subsequent sort. Alternatively, an automated version of the DIS similarity sort could be applied which relies on a recursive technique of sequentially picking a reference spectrum, finding the next 'closest' spectrum, replacing the reference spectrum with the latter, and then repeating this process until all spectra are exhausted. This top-to-bottom process (which creates the sorted contour plot) scales better than an $N^2$ process, where there are N total spectra.

$$\prod_{i=1}^{N} (N-i), \qquad \text{Equation 7}$$

Like the single pass algorithm above, spectra are compared for similarity in this recursive process by an SSD function that yields a single metric:

$$SSD = \sum_i (P_D[i] - P_T[i])^2, \quad \text{Equation 8}$$

where i counts through each spectral channel as the spectrum currently under evaluation ($P_D$) is compared with the last spectrum ($P_T$) sorted into the contour plot.

In a simple SSD calculation of the 7-channel spectra, each channel is equally weighted. However, one could design weighting factors dependent on probe specificities. Since SSD can be calculated between any two spectra, it is of great interest to determine how the SSD distance relates to phylogenetic distances. In a perfect case, we would find an isomorphic mapping between the spectral distances and the phylogenetic distances, as suggested in FIG. 16.

Figure 16:
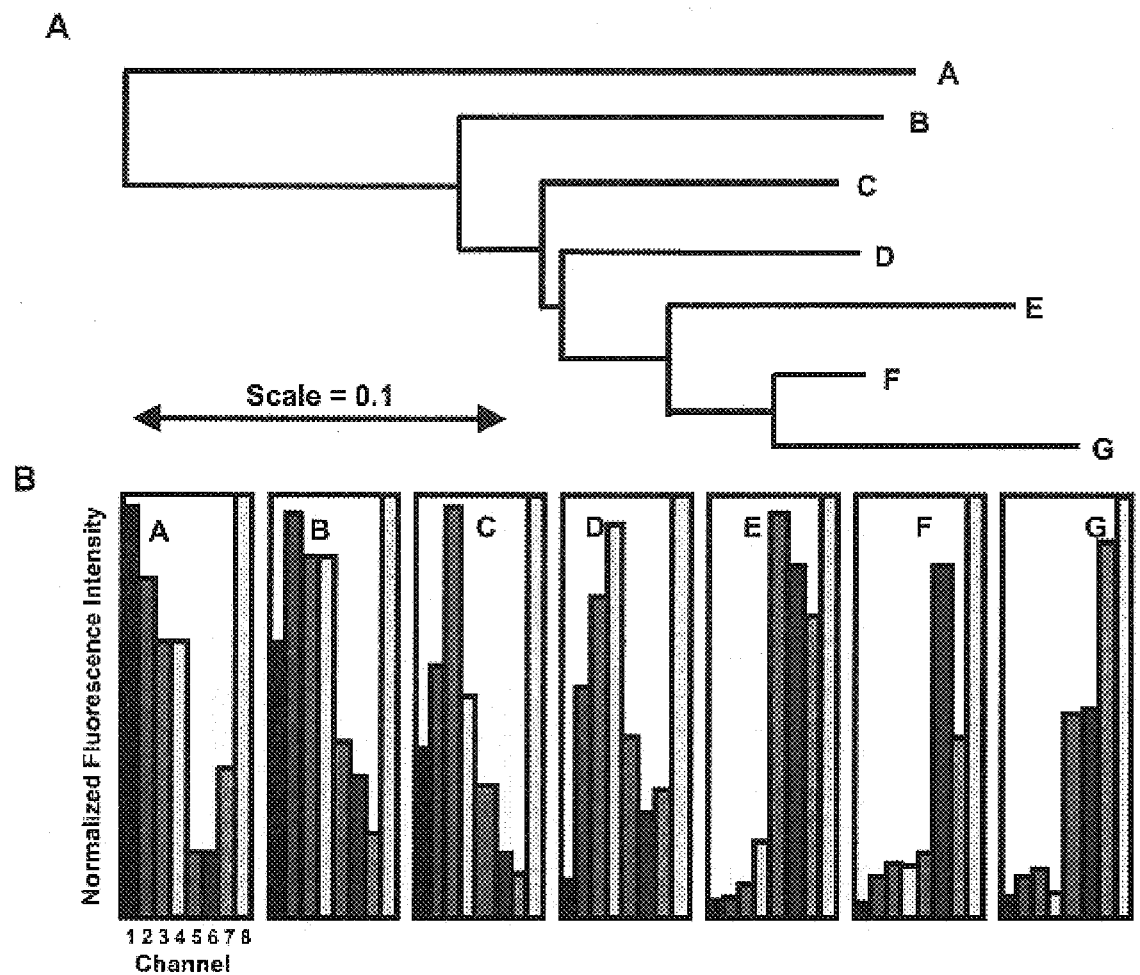
FIG. 16A (top) Actual phylogenetic tree for the bacterial and archaeal samples listed in FIG. 15.
FIG. 16B (bottom), hypothetical MTID fingerprints from an 8-channel analysis. The histograms are meant to represent the outcome of a hybridization experiment using a set of 7 species-specific probes (labeled A–G) and one universal probe. The measured intensity for each fluorescent dye/probe combination is represented by the height of the vertical color bars. Note that channel 8, which measures the signal from the universal ("all ribosome") probe, has been used to normalize all of the fingerprints for variability in the amount of target rRNA, dye quantum efficiency, and the spectral response of the instrument. The hypothetical intensity values shown here approximately follow phylogeny. The phylogenetic tree (adapted from Olsen et al., 1994) is based on maximum likelihood analysis of the complete 16S RNA sequences. Key for bacteria: A, *Halobacterium halobium*; B, *Chloroflexus aurantiacus*; C, Synechococcus PCC 6301; D, *Bacillus subtilis*; E, *Rhodobacter capsulatus*; F, *Chromatium vinosum*; G, *Escherichia coli*. The distance scale represents 0.1 changes per sequence position.

The top portion of FIG. 16 shows the phylogenetic tree for the bacterial and archaeal samples listed in FIG. 15. This tree was constructed using a maximum likelihood analysis of the complete 16S RNA. The bottom portion shows hypothetical MTID fingerprints from an 8-channel analysis. The histograms represent the outcome of a hybridization experiment using a set of 7 species-specific probes (labeled A–G) and one universal probe. The measured intensity for each fluorescent dye/probe combination is represented by the height of the vertical color bars. Note that channel 8, which measures the signal from the universal ('all ribosome') probe, has been used to normalize all channel spectra. Although hypothetical intensity values are shown here, simulations of the data have been conducted using known equations to calculate the $T_m$ of a given probe when it is bound to any specific sequence (for example, from the organisms of FIG. 15). These $T_m$'s can be used to calculate the extent of binding of the probe to each organism under specified wash conditions. Using these equations, we can also deduce the percentage of probes that will hybridize to the 16S rRNA relative to each other and relative to the universal probe. Thus there is an isomorphic mapping between the phylogenetic tree distances and the MTID hybridization pattern. To cover a broad range of stringencies and differing phylogenetic breadths, it can be important to use probe mixtures consisting of multiple probes per each of the fluorophores as shown in Tables 5 & 6.

Probe ensembles can be designed using algorithms to construct individual probes which target large taxa of bacteria. The probes for each taxonomic group can be labeled with a unique dye or combination of dyes. Ideally a taxonomic probe should match the 16S ribosomal sequence of every species in that group and not a single species outside that group. Unfortunately an ideal taxonomic probe is rarely possible. In order to overcome this problem we can use, for example, ensembles of 6 to 10 probes for each of four phyla (Archea/Euryarchaeota, Proteobacteria/gamma subdivision, Bacteriodes/Cytophaga/Flexibacter, and Actinobacteria) where each individual probe recognizes 60 to 90% of the target species. We developed software to aid in probe design, which produces a consensus sequence for any number of 16S sequences. This program takes a parameter that represents a cutoff for the percentage of the sequences that must contain any particular base in order for it to be included in the consensus sequence. Since these probes are to be used simultaneously they must have similar melting temperatures ($T_m$). Therefore we have also implemented software, based on the nearest neighbor model for calculating the $T_m$ which when given a potential sequence indicates which subsequence should be used to fit the required $T_m$ range.

For three of our taxonomic probe ensembles, approximately the same number of probes should hybridize to each species belonging to that phylum. However the Proteobacteria/gamma subdivision probes were designed to be more heavily weighted in the enterics family by incorporating more sequences from this group. Although the species from which the consensus sequence was derived belong to Proteobacteria gamma, we included several probes that also matched the other subdivisions of Proteobacteria. When hybridized to bacteria, the Proteobacteria probe ensemble results in a series of intensities depending on the species phylogenetic distance from the enterics family. Typically non-gamma Proteobacteria, gamma and enterics bind 2 or 3, 4 to 7 and 9 or 10 probes, respectively. By normalizing the intensity of the taxonomic probe ensemble channel to the universal probe channel it is therefore possible to determine the approximate taxonic position of an unknown bacterium in the Proteobacteria phylogenetic tree.

We have tested all four probe ensembles simultaneously on over 15 different species and found that their behavior fully conforms to our expectations. We have also used them in combination with species specific probes to identify a single species in a complex mix of bacteria. It should be noted that corrections for bleed between channels and normalization (Equations 1–5) relative to the universal probe are critical in these experiments especially for probe ensembles that produce the (above-mentioned) phylogenetic intensity gradient.

Another method that can be used to generate phylogenetic probes is bacterial chromosome painting (Lanoil & Giovannoni, 1997). In this method, fluorescently labeled fragments of the entire bacterial genome are generated by nick translation (Kelly et al., 1970) and used as probes. Genomic DNA is isolated from eight different culturable organisms that are chosen to represent the entire phylogenetic tree or sections of the tree. The purified DNA is digested with DNase I so that fragments of 50–200 base pairs are created, as determined by agarose gel electrophoresis. The fragments are then labeled using *E. coli* DNA polymerase I and a mixture of deoxynucleotides containing fluorescently tagged dCTP. Each genomic DNA probe set is labeled with a different fluorescent tag, such as those listed in FIG. 23. The labeled probes are then purified in a microconcentrator and stored at –20° C.

A sample of target cells (consisting of either unknown organisms to be identified or a standard set of the eight organisms from which the probes were generated) is washed, fixed with formalin, and attached to a glass slide. The sample is then treated with lysozyme, RNase A, and pepsin (with intervening washes) to remove RNA and permeabilize the cells. They are then washed, dehydrated in an ethanol series, and air-dried. The target DNA inside the cells is then denatured by incubating the slides in buffer containing 70% formamide at 80° C. Finally, the slides are dehydrated again and air-dried. The probe DNA (200 ng) is mixed with sheared calf thymus DNA, dried, and resuspended in 100% formamide. Dextran sulfate in buffer is added to resuspend the probe DNA, and the mix is briefly heated to 80° C. and then chilled on ice to fully denature the probes. The denatured probes are then spotted onto the slide containing the fixed target cells. The spot is covered with a coverslip, sealed with rubber cement, and allowed to incubate at 37° C. for two days. After removing the coverslip, the slide is washed at 50° C. and then at room temperature for 5–10 min. The slide is then washed in low ionic strength buffer pre-heated to 65° C. (or an appropriate temperature to achieve the desired wash stringency). The slide is then washed several more times at decreasing temperature (down to room temperature) and decreasing incubation time. The cells are then treated with anti-fade compound and permanently sealed under a glass coverslip.

Images of the labeled target cells (both unknowns and standards) are taken at eight different wavelengths. The intensity of the fluorescence emission from the unknown cells in each spectral channel is compared to the intensity of the standards. A spectral fingerprint is thereby generated for each unknown cell and each standard. The intensity can then be mapped onto the known phylogenetic distance between the standards to estimate the location of each unknown in the phylogenetic tree as described above. The advantage of using chromosome paints is that the probes do not need to be rationally designed, and their sequence complexity is high.

EXAMPLE 6

Multi-spectral Identification Using Fluorescently Labeled Antibodies

Another method that is capable of identifying cells with high specificity involves antibodies directed against particular target molecules. These targets may include, for example, cell surface antigens, oligonucleotide probes hybridized to DNA or RNA, or intracellular proteins. There are a great number of antibodies that have been designed to identify particular species and sub-species of bacteria as well as numerous viruses and eukaryotic cell types. Many of these antibodies are available from commercial suppliers, such as Research Diagnostics (Flanders, N.J.). Antibodies are particularly useful for identifying particular serotypes of bacteria, such as E. coli O157:H7 (Tortorello et al., 1998; Seo & Frank, 1999; Pyle et al., 1999). They can also be used to identify specific haptens that are covalently attached to oligonucleotide probes. Such haptens include digoxigenin, fluorescein, bromodeoxyuridine, and biotin. Hapten-directed antibodies are often used to assay for in situ PCR products (described in the next example).

Antibody detection via immunofluorescence staining can be visualized by two different methods. Indirect visualization employs a secondary antibody with an attached enzyme, such as alkaline phosphatase. By adding a precipitating fluorogenic substrate, such as the ELF-phosphate substrate from Molecular Probes (Eugene, Oreg.), the location of the antibody can be visualized by the fluorescence emission of the insoluble product of the enzyme reaction. Each fluorescent color therefore requires a separate enzyme and substrate combination. Direct visualization, which provides a less intense signal but is easier to perform, involves labeling an antibody with multiple copies of a fluorescent label. Labeling can be done by reacting the purified antibody with a fluorophore that contains a chemically reactive group, such as an N-hydroxysuccinimidyl (NHS) ester. This particular reagent reacts specifically with free amino groups on proteins to form a covalent bond. The unreacted label can then be separated from the labeled antibody by column chromatography.

After the target cells have been incubated in the presence of the antibodies, the cells are thoroughly washed with buffer to remove any unbound antibody probes. In the case of intracellular protein targets, the target cells may need to be permeabilized to permit entry of the antibodies. For direct visualization, up to eight different antibodies labeled with eight distinct fluorophores are simultaneously used. Antibody detection can also be combined with the fluorescently labeled oligonucleotide probes described above. The MTID system is then used to image the labeled target cells. Image stacks are acquired at the appropriate wavelengths, overlap corrections are made, and the pixels are sorted by their spectral fingerprints. These data are then used to automatically classify the cells based on their spectra.

EXAMPLE 7

Multi-Spectral Identification Using In Situ PCR

In situ PCR is a relatively new method for cellular identification that provides tremendous flexibility because it allows the entire DNA genome (as well as mRNA and rRNA, via reverse transcriptase PCR) to be used as a target. Normally, targets such as genes within the chromosomal or organellar DNA and many mRNA transcripts are present in too few copies to be detected by simple probing and imaging of single cells. However, by using oligonucleotide primers that bind specifically to particular target sequences, the target sequences can be selectively amplified. In situ PCR thus provides an enormous variety of potential target sequences for identification. PCR amplification provides enough secondary DNA target to allow probing by nucleic acid or protein/antibody probes. Or, if fluorescently labeled nucleotides are directly incorporated into the PCR product, the fluorescence emission of the PCR product can be detected. In situ PCR is useful for detecting bacteria and viruses in infected tissue and individual cells, as well as for identifying cells having abnormal genotypes. In this example, we describe how the MTID system can be employed to exploit this sequence diversity more effectively.

In situ PCR on bacterial cells is performed as described in published reports (Hodson et al., 1995; Tani et al., 1998). Briefly, the target cells are fixed, washed, attached to slides, and air-dried. The cells are then dehydrated. Following this step, they are permeabilized with lysozyme and proteinase K and treated with DNase-free RNase to remove RNA. The cells are then washed in buffer and dehydrated again. They are then sealed under glass with PCR buffer, nucleotides, multiple sets of primers, and DNA polymerase. Each PCR cycle consists of 30 s of denaturation at 94° C., 30 s of annealing (at a temperature appropriate for the primer sets), and 60 s of extension at 72° C. The amplification is repeated for 30 cycles in a temperature-controlled thermal cycler. When the reactions are complete, the sample is air-dried, treated briefly with proteinase K (3 min), and then washed with distilled water.

There are a number of ways to obtain DNA sequences for each of the primer pairs, and a number of strategies for employing multispectral sets of primers. Probe sequences can be derived from whole genome or partial genome sequencing, or sequencing of MRNA. DNA sequences can also be deduced from protein sequencing. Degenerate or phylogenetic probe sets can also be designed based on alignment of sequence families. Primer sets can thus be designed to target particular groups of enzyme genes, for example. It is also possible to target all of the different primer pairs to a single species, group of species, or cell type in order to detect the presence or absence of entire sets of sequences. In addition to detecting entire genes, one could also use probes at high stringency to detect, for example, multiple single-nucleotide polymorphisms. This type of analysis can provide fairly detailed genomic profiling in situ.

To perform multi-spectral identification in a one-step PCR reaction, one may tag only the primer pairs, each with a given hapten (e.g., biotin, digoxigenin, fluorescein, rhodamine, bromodeoxyuridine). Note that fluorescein and rhodamine are also fluorophores. However, this may not provide enough hapten for the antibody or enough fluorescence to detect. To incorporate additional hapten into the products, the nucleotide mix can include approximately 10% tagged nucleotides. However, this means that the annealing and synthesis reactions must be run sequentially for each template/primer combination, to avoid mixing the products. For direct fluorescence detection of the PCR products, the nucleotide mix may contain fluorescently labeled nucleotides. The hapten-labeled products can be detected by immunofluorescence staining with fluorescently labeled antibodies or by enzyme-conjugated secondary antibodies that bind to a primary antibody which recognizes a given hapten. Each aliquot of fluorescently labeled antibody is labeled by reacting it with the NHS ester of a given fluorophore. For example, the fluorophores in FIG. 23 can be used.

Image stacks are the be obtained as described above for the rRNA probes, and the spectral fingerprints of each cell are be acquired, corrected and sorted to identify them based on the primers that were used to amplify their sequence. Up to now, the in situ PCR method has not been used with multiple primer pairs on the same sample, or with multi-spectral detection. Combining in situ PCR with the MTID system permits higher throughput and more sophisticated analysis due to simultaneous detection of multiple sequences in single cells.

EXAMPLE 8

MTID Cryogenics

Fluorescent tagging technology is ultimately limited by the number of fluorescent markers that can be uniquely identified by currently available fluorescence imaging instrumentation. The MTID instrument can include a cryogenic stage for low-temperature imaging. Here we describe the construction of a stage that can be cooled to 77 K. Cryogenic imaging at such temperatures will enable us to achieve greater separation of the fluorophores within a dye set. Maximal differentiation of individual spectra is expected to be better resolved due to peak sharpening and increased fluorescence quantum yields.

Figure 17:
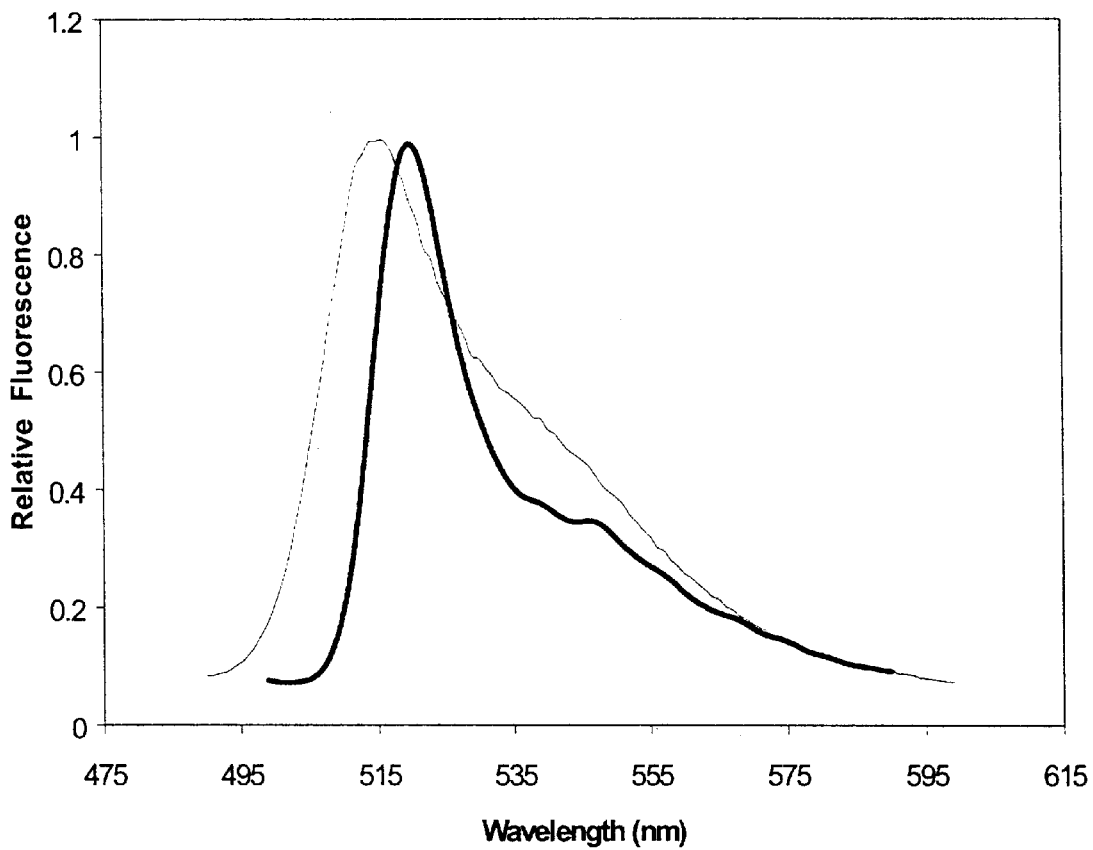
FIG. 17 Fluorescence emission spectrum of latex beads containing a fluorescein-like compound recorded at 300 K (thin line) and 77K (thick line). Cryogenic temperatures have red-shifted this band by ~10 nm and reduced the full-width-at-half-maximum (FWHM) by ~2-fold.

In general, the absorption, fluorescence excitation, and fluorescence emission bands of complex organic molecules narrow with decreasing temperature because of decreases in the vibrational broadening of the electronic ground-state ($S_0$) and first-excited singlet state ($S_1$). Typical fluorophores such as fluorescein have an almost mirror-image symmetry about a 'zero-point crossing' where the vibrational energy of the $S_0$ and $S_1$ states are equivalent (Klessinger & Michl, 1995). At this zero-point crossing, the wavelength of the absorbed and re-emitted photon is indistinguishable. However, the overall shape of the absorption (or excitation) band and the emission band cannot be predicted from the structure of the organic molecules involved (Turro, 1991). Selection rules and Franck-Condon factors are also involved. The Kennard-Stepanov relationship (Björn & Björn, 1986; Sauer et al., 1996) has been used to introduce a Boltzmann factor to predict such effects; this has recently been extended to include FRET pairs with some success (Tomita et al., 1996). While there is a general tendency for bands to sharpen dramatically at cryogenic temperatures, this phenomenon is not fully predictable. See FIG. 17.

It is also generally the case for organic fluorophores that the fluorescence quantum yield increases with decreasing temperature down to ~100 K (Turro, 1991). The simplest and most general cause for this effect is that nonradiative decay pathways are blocked to an increasing extent in rigid molecules (Klessinger & Michl, 1995). One striking example of this phenomenon is a recent mutant of the Green Fluorescent Protein (GFP) engineered by KAIROS and dubbed 'Org 18' (Kummer et al., 1998). GFP, which bears a genetically encoded fluorophore, is highly fluorescent at room temperature. However, in Org 18 the isolated protein is chromogenic (orange) at room temperature and fluorescent green only at cryogenic temperatures. This is due to the fact that the molecule locks into a rigid conformation at low temperatures. Other common examples are known wherein chromogenic substances become fluorogenic when constrained (Turro, 1991). A typical case is the dye methylviologen, which becomes fluorescent upon adsorption to glass. The number of fluorophores that are commonly used in cell biology can be expanded to include substances that are merely chromogenic at room temperature since wavelength shifts and peak sharpening of such dyes may become useful only at cryogenic temperatures.

An additional physicochemical factor must be considered during optimization of different dye sets: In complex mixtures of fluorescent molecules that are within the distance at which dipole-dipole interactions become significant (~50 Å), energy transfer can occur as predicted by the Förster equations (Förster, 1948). Förster energy transfer (i.e., FRET) requires spectral overlap between the fluorescence emission spectrum of a donor molecule and the absorption spectrum of an acceptor molecule, as represented by the spectral overlap integral, J:

$$J(\lambda) = \int f(\lambda)\epsilon_A(\lambda)\lambda^4 d\lambda \qquad \text{Equation 9}$$

The value of J is graphically equivalent to the integrated area shared between the donor's fluorescence emission spectrum and the acceptor's ground state absorption spectrum, both normalized to unity. It then follows that as absorption and fluorescence emission bands become narrower at cryogenic temperatures, the value of the J decreases. This substantially reduces FRET because the efficiency of energy transfer is directly proportional to J (Govindjee & Satoh, 1986). Thus, one can attempt to reduce or eliminate some of the FRET coupling which might occur in a specific set of fluorophores. This would greatly simplify the problem of identifying and quantitating signals arising from individual members of the set.

Cryogenic measurements require incorporation of a cryogenic stage to the MTID instrument. This comprises a cryogenic heat sink (14, FIG. 3) insulated on 5 of its 6 sides; the conductive side consists of a small (1 $cm^2$) black-anodized cold finger that is in direct contact with the sample slide. Other components are required to heat the objective and to prevent condensation. These include an objective heater (15, FIG. 3) that is commercially available (Bioptechs, Inc.), a dry nitrogen source nozzle (19, FIG. 3), heat sink (14, FIG. 3), and liquid nitrogen (LN2) supply, that may be fabricated by a machinist.

REFERENCES

Adal, K. A., Cockerell, C. J. & Petri, W. A. (1994) Cat scratch disease, bacillary angiomatosis, and other infections due to Rochalimaea. *N. Engl. J. Med.* 330:1509–1515.

Altschul, S. F., Madden, T. L., Schaffer, A. A., Zhang, J., Zhang, Z., Miller, W. & Lipman, D. J. (1997) Gapped BLAST and PSI-BLAST: a new generation of protein database search programs. *Nucleic Acids Res.* 25:3389–3402.

Amann, R. I., Krumholz, L. & Stahl, D. A. (1990) Fluorescent-oligonucleotide probing of whole cells for determinative, phylogenetic, and environmental studies in microbiology. *J. Bacteriol.* 172:762–770.

Amann, R. I., Stromley, J., Devereux, R., Key, R. & Stahl, D. A. (1992) Molecular and microscopic identification of sulfate-reducing bacteria in multispecies biofilms. *Appl. Environ. Microbiol.* 58:614–623.

Amann, R. I., Ludwig, W. & Schleifer, K.-H. (1995) Phylogenetic identification and in situ detection of individual microbial cells without cultivation. *Microbiol. Rev.* 59:143–169.

Amsel, R., Totten, P. A., Spiegel, C. A., Chen, K. C. S., Eschenbach, D. A. & Holmes, K. K. (1983) Nonspecific vaginitis. Diagnostic criteria and microbial and epidemiologic associations. *Am. J. Med.* 73:14–22.

Andersen, B. M. (1995) Biochemical profiles and serotypes of nosocomial *Enterobacter cloacae* strains in Northern Norway: Biochemical identification problems with commercial test systems. *Infection* 23:339–343.

Barns, S. M., Delwiche, C. F., Palmer, J. D. & Pace, N. R. (1996) Perspectives on archaeal diversity, thermophily and monophyly from environmental rRNA sequences. *Proc. Natl. Acad. Sci. USA* 93:9188–9193.

Birnbaum, D., Herwaldt, L., Low, D. E., Noble, M., Pfaller, M., Sherertz, R. & Chow, A. W. (1994) Efficacy of microbial identification system for epidemiologic typing of coagulase-negative staphylococci. *J. Clin. Microbiol.* 32:2113–2119.

Björn, L. O. & Björn, G. S. (1986) *Photochem. Photobiol.* 44:535–542.

Chan, W. C. & Nie, S. (1998) Quantum dot bioconjugates for ultrasensitive nonisotopic detection. *Science* 281:2016–2018.

DeLong, E. F., Wickham, G. S. & Pace, N. R. (1989) Phylogenetic stains: ribosomal RNA-based probes for the identification of single cells. *Science* 243:1360–1363.

De Saizieu, A., Certa, U., Warrington, J., Gray, C., Keck, W. & Mous, J. (1998) Bacterial transcript imaging by hybridization of total RNA to oligonucleotide arrays. *Nature Biotechnology* 16:45–48.

Dubiley, S., Kirillov, E., Lysov, Y. & Mirzabekov, A. (1997) Fractionation, phosphorylation and ligation on oligonucleotide microchips to enhance sequencing by hybridization. *Nucleic Acids Res.* 25:2259–2265.

Eschenbach, D. A. (1993) Bacterial vaginosis and anaerobes in obstetric-gynecologic infection. *Clin. Infect. Dis.* 16(Suppl. 4):S282–S287.

Felsenstein, J. (1988) Phylogenies from molecular sequences: inference and reliability. *Annu. Rev. Genet.* 22:521–565.

Felsenstein, J. (1989) Phylogeny inference package (version 3.2). *Cladistics* 5:164–166.

Fink, W. L. (1986) Microcomputers and phylogenetic analysis. *Science* 234:1135–1139.

Fredricks, D. N. & Relman, D. A. (1996) Sequence-based identification of microbial pathogens: a reconsideration of Koch's postulates. *Clin. Microbiol. Rev.* 9:18–33.

Gardner, H. L. & Dukes, C. D. (1955) *Haemophilus vaginalis* vaginitis. A newly defined specific infection previously classified "nonspecific" vaginitis. *Am. J. Obstet. Gynecol.* 69:962–976.

Giovannoni, S. J., DeLong, E. F., Olsen, G. J. & Pace, N. R. (1988) Phylogenetic group-specific oligodeoxynucleotide probes for identification of single microbial cells. *J. Bacteriol.* 170:720–726.

Govindjee & Satoh, K. (1986) In: *Light Emission by Plants and Bacteria* (Govindjee, Amesz, J. & Fork, D. C., eds.) Academic Press, Orlando, pp. 497–537.

Gunderson, J. H. & Goss, S. H. (1997) Fluorescently-labeled oligonucleotide probes can be used to identify protistan food vacuole contents. *J. Euk. Microbiol.* 44:300–304.

Head, I. M., Saunders, J. R. & Pickup, R. W. (1998) Microbial evolution, diversity, and ecology: A decade of ribosomal RNA analysis of uncultured microorganisms. *Microb. Ecol.* 35:1–21.

Hillier, S. L., Krohn, M. A., Rabe, L. K., Klebanoff, S. J. & Eschenbach, D. A. (1993) The normal vaginal flora, $H_2O_2$-producing lactobacilli, and bacterial vaginosis in pregnant women. *Clin. Infect. Dis.* 16(Suppl. 4):S273–S281.

Hilton, D. A., Love, S., Goodwin, T. & Pringle, J. H. (1994) Demonstration of mitochondrial ribosomal RNA in frozen and paraffin-embedded sections of skeletal muscle by in situ hybridization. *Neuropathol. Appl. Neurobiol.* 20:573–576.

Hodson, R. E., Dustman, W. A., Garg, R. P. & Moran, M. A. (1995) In situ PCR for visualization of microscale distribution of specific genes and gene products in prokaryotic communities. *Appl. Environ. Microbiol.* 61:4074–4082.

Hoheisel, J. D. (1997) Oligomer-chip technology. *Trends Biotechnol.* 15:465–469.

Hugenholtz, P., Pitulle, C., Hershberger, K. & Pace, N. R. (1998a) Novel division level bacterial diversity in a Yellowstone hot spring. *J. Bacteriol.* 180:366–376.

Hugenholtz, P., Goebel, B. M. & Pace, N. R. (1998b) Impact of culture-independent studies on the emerging phylogenetic view of bacterial diversity. *J. Bacteriol.* 180:4765–4774.

Kelly, R. B., Cozzarelli, N. R., Deutscher, M. P., Lehman, I. R. & Kornberg, A. (1970) Enzymatic synthesis of deoxyribonucleic acid. XXXII. Replication of duplex deoxyribonucleic acid by polymerase at a single strand break. *J. Biol. Chem.* 245:39–45.

Klessinger, M. & Michl, J. (1995) *Excited States and Photochemistry of Organic Molecules*, VCH Publishers, New York.

Kummer, A. D., Kompa, C., Lossau, H., Pollinger-Dammer, F., Michel-Beyerle, M. E., Silva, C. M., Bylina, E. J., Coleman, W. J., Yang, M. M. & Youvan, D. C. (1998) *Chemical Physics* 237: 183–193.

Labidi, B., Broders, F., Meyer, J. L. & Hernandez-Verdun, D. (1990) Distribution of rDNA and 28S, 18S, and 5S rRNA in micronuclei containing a single chromosome. *Biochem. Cell. Biol.* 68:957–964.

Lanoil, B. D. & Giovannoni, S. J., (1997) Identification of bacterial cells by chromosomal painting. *Applied Environ. Microbiol.* 63:1118–1123.

Lim, E. L., Amaral, L. A., Caron, D. A. & DeLong, E. F. (1993) Application of rRNA-based probes for observing marine nanoplanktonic protists. *Appl. Environ. Microbiol.* 59:1647–1655.

Lorber, B. (1996) Are all diseases infectious? *Ann. Intern. Med.* 125:844–851.

Maidak, B. L., Olsen, G. J., Larsen, N., Overbeek, R., McCaughey, M. J. & Woese, C. R. (1997) The RDP (Ribosomal Database Project). *Nucleic Acids Res.* 25:109–111.

Medlin, L., Elwood, H. J., Stickel, S. & Sogin, M. L. (1988) The characterization of enzymatically amplified eukaryotic 16S-like rRNA-coding regions. *Gene* 71:491–499.

Muli, F. & Struthers, J. K. (1998) Use of a continuous-culture biofilm system to study the antimicrobial susceptibilities of *Gardnerella vaginalis* and *Lactobacillus acidophilus*. *Antimicrob. Agents Chemother.* 42:1428–1432.

Müller, C., Stain, C. & Burghuber, O. (1993) *Tropheryma whippelii* in peripheral blood mononuclear cells and cells of pleural effusion [Letter]. *Lancet* 341:701.

Muyzer, G. & Smalla, K. (1998) Application of denaturing gradient gel electrophoresis (DGGE) and temperature gradient gel electrophoresis (TGGE) in microbial ecology. *Antonie Van Leeuwenhoek* 73:127–41.

Nederlof, P. M., van der Flier, S., Vrolijk, J., Tanke, H. J. & Raap, A. K. (1992) Fluorescence ratio measurements of double-labeled probes for multiple in situ hybridization by digital imaging microscopy. *Cytometry* 13:839–845.

Neidhardt, F. C. (1987) Chemical composition of *Escherichia coli*. In: *Escherichia coli and Salmonella typhimurium* (Neidhardt, F. C. et al., eds.) Vol 1, pp. 3–6. American Society for Microbiology, Washington, D.C.

Ng, W. L., Schummer, M., Cirisano, F. D., Baldwin, R. L., Karlan, B. Y. & Hood, L. (1996) High-throughput plasmid mini preparations facilitated by micro-mixing. *Nucleic Acids Res.* 24:5045–5047.

Nübel, Ü., Garcia-Pichel, F., Kühl, M. & Muyzer, G. (1999) Quantitative microbial diversity: Morphotypes, 16S RNA genes, and carotenoids of oxygenic phototrophs in microbial mats. *Appl. Environ. Microbiol.* 65:422–430.

O'Hara, C. M., Tenover, F. C. & Miller, J. M. (1993) Parallel comparison of accuracy of API 20E, Vitek GNI, MicroScan Walk/Away Rapid ID, and Becton Dickinson Cobas Micro ID-E/NF for identification of members of the family Enterobacteriaceae and common gram-negative, non-glucose-fermenting bacilli. *J. Clin. Microbiol.* 31:3165–3169.

Olsen, G. J., Lane, D. J., Giovannoni, S. J., Pace, N. R. & Stahl, D. A. (1986). Microbial ecology and evolution: a ribosomal RNA approach. *Annu. Rev. Microbiol.* 40:337–365.

Olsen, G. J., Woese, C. R. & Overbeek, R. (1994) The winds of (evolutionary) change: Breathing new life into microbiology. *J. Bacteriol.* 176:1–6.

Osterhout, G. J., Shull, V. H. & Dick, J. D. (1991) Identification of clinical isolates of gram-negative nonfermentative bacteria by an automated cellular fatty acid identification system. *J. Clin. Microbiol.* 29:1822–1830.

Pace, N. R., Stahl, D. A., Lane, D. L. & Olsen, G. J. (1986). The analysis of natural microbial populations by rRNA sequences. *Adv. Microb. Ecol.* 9:1–55.

Pace, N. R. (1997) A molecular view of microbial diversity and the biosphere. *Science* 276:734–740.

Porter, J., Edwards, C., Morgan, J. A. W. & Pickup, R. W. (1993) Rapid, automated separation of specific bacteria from lake water and sewage by flow cytometry and cell sorting. *Applied Environ. Microbiol.* 59:3327–3333.

Potera, C. (1999) Forging a link between biofilms and disease (News Focus). *Science* 283:1837–1839.

Priestley, C. J. F. & Kinghorn, G. R. (1996) Bacterial vaginosis. *Br. J. Clin. Pract.* 50:331–334.

Pyle, B. H., Broadway, S. C. & McFeters, G. A. (1999) Sensitive detection of *Escherichia coli* O157:H7 in food and water by immunomagnetic separation and solid-phase laser cytometry. *Appl. Environ. Microbiol.* 65:1966–1972.

Rappé, M. S., Suzuki, M. T., Vergin, K. L. & Giovannoni, S. J. (1997) Phylogenetic diversity of ultraplankton plastid small-subunit rRNA genes recovered in environmental nucleic acid samples from the Pacific and Atlantic. coasts of the United States. *Applied Environ. Microbiol.* 64:294–303.

Relman, D. A., Schmidt, T. M., MacDermott, R. P. & Falkow, S. (1992) Identification of the uncultured bacillus of Whipple's disease. *N. Engl. J. Med.* 327:293–301.

Relman, D. A. (1998) Detection and identification of previously unrecognized microbial pathogens. *Emerg. Infect. Dis.* 4:382–389.

Restaino, L., Frampton, E. W., Irbe, R. M. & Allison, D. R. (1997) A 5-h screening and 24-h confirmation procedure for detecting *Escherichia coli* O157:H7 in beef using direct epifluorescent microscopy and immunomagnetic separation. *Lett. Appl. Microbiol.* 24:401–404.

Rice, J., O'Connor, C. D., Sleigh, M. A., Burkill, P. H., Giles, I. G. & Zubkov, M. V. (1997) Fluorescent oligonucleotide rDNA probes that specifically bind to a common nanoflagellate, *Paraphysomonas vestita*. *Microbiology* 143:1717–1727.

Rickman, L. S., Freeman, W. R., Green, W. R., Feldman, S. T., Sullivan, J., Russack, V. & Relman, D. A. (1995) Brief report: Uveitis caused by *Tropheryma whippelii* (Whipple's bacillus). *N. Engl. J. Med.* 332:363–366.

Ried, T., Baldini, A., Rand, T. C. & Ward, D. C. (1992) Simultaneous visualization of seven different DNA probes by in situ hybridization using combinatorial fluorescence and digital imaging microscopy. *Proc. Natl. Acad. Sci. U.S.A.* 89:1388–1392.

Sauer, K., Cogdell, R. J., Prince, S. M., Freer, A. A., Isaacs, N. W. & Scheer, H. (1996) *Photochem. Photobiol.* 64:564.

Schrenk, M. O., Edwards, K. J., Goodman, R. M., Hamers, R. J. & Banfield, J. F. (1998) Distribution of thiobacillus ferrooxidans and leptospirillum ferrooxidans: implications for generation of acid mine drainage. *Science* 279:1519–1522.

Schröck, E., du Manoir, S., Veldman, T., Schoell, B., Wienberg, J., Ferguson-Smith, M. A., Ning, Y., Ledbetter, D. H., Bar-Am I., Soenksen, D., Garini, Y. & Ried, T. (1996) Multicolor spectral karyotyping of human chromosomes. *Science* 273:494–497.

Seo, K. H. & Frank, J. F. (1999) Attachment of *Escherichia coli* O157:H7 to lettuce leaf surface and bacterial viability in response to chlorine treatment as demonstrated by using confocal scanning laser microscopy. *J. Food Prot.* 62:3–9.

Short, J. (1997) Recombinant approaches for accessing biodiversity. *Nat. Biotechnol.* 15:1322–1323.

Shuman, S. (1994) Novel approach to molecular cloning and polynucleotide synthesis using vaccinia DNA topoisomerase. *J. Biol. Chem.* 269:32678–32684.

Sparks, J. M. (1991) Vaginitis. *J. Reprod. Med.* 36:745–752.

Speicher, M. R., Ballard, S. G. & Ward, D. C. (1996) Karyotyping human chromosomes by combinatorial multi-fluor FISH. *Nature Genet.* 12:368–375.

Strunk, O., Gross, O., Reichel, B., May, M., Hermann, S., Struckmann, N., Nonhoff, B., Lenke, M., Vilbig, A., Ludwig, T., Bode, A., Schleifer, K. -H. & Ludwig, W. (1996) ARB: A software environment for sequence data. [Online] http://www.mikro.biologie.tu-muenchen.de/pub/ARB.

Sugimoto, N., Nakano, S., Katoh, M., Matsumura, A., Nakamuta, H., Ohimichi, T., Yoneyama, M. & Sasaki, M. (1995) Thermodynamic parameters to predict stability of RNA/DNA hybrid duplexes. *Biochemistry* 34:11211–11216.

Tani, K., Kurokawa, K. & Nasu, M. (1998) Development of a direct in situ PCR method for detection of specific bacteria in natural environments. *Appl. Environ. Microbiol.* 64:1536–1540.

Tanner, M. A., Goebel, B. M., Dojka, M. A., Pace, N. R. (1998). Specific ribosomal DNA sequences from diverse environmental settings correlate with experimental contaminants. *Applied and Environmental Microbiology* 64:3110–3113.

Tanner, M. A., Shoskes, D., Shahed, A. & Pace, N. R. (1999) Prevalence of corynebacterial 16S rRNA sequences in patients with bacterial and "nonbacterial" prostatitis. *J. Clin. Microbiol.* 37: 000-000 (In Press).

Tomita, A., Shah, J. & Knox, R. S. (1996) *Phys. Rev. B* 53:10793–10803.

Tortorello, M. L., Reineke, K. F., Stewart, D. S. & Raybourne, R. B. (1998) Comparison of methods for determining the presence of *Escherichia coli* O157:H7 in apple juice. J. Food Prot. 61:1425–1430.

Turro, N. J. (1991) *Modern Molecular Photochemistry*, University Science Books, Mill Valley, Calif.

Vandamme, E. J. (1994) The search for novel microbial fine chemicals, agrochemicals and biopharmaceuticals. *J. Biotechnol.* 37:89–108.

Vandamme, P. (1996) Polyphasic taxonomy, a consensus approach to bacterial systematics. *Microbiol. Rev.* 60:407–438.

Wallner, G., Amann R. & Beisker, W. (1993) Optimizing fluorescent in situ hybridization with rRNA-targeted oligonucleotide probes for flow cytometric identification of microorganisms. *Cytometry* 14:136–143.

Ward, D. M., Bateson, M. M., Weller, R. & Ruff-Roberts, A. L. (1992) Ribosomal RNA analysis of microorganisms as they occur in nature. In: *Advances in Microbial Ecology* (Marshall, K. C., ed.) pp. 219–286, Plenum Press, New York.

Weisburg, W. G., Barns, S. M., Pelletier, D. A. & Lane, D. J. (1991) 16S ribosomal DNA amplification for phylogenetic study. *J. Bacteriol.* 173:697–703.

Welsh, J. & McClelland, M. (1990) Fingerprinting genomes using PCR with arbitrary primers. *Nucleic Acids Res.* 24:7213–7218.

Williams, J. G. K., Kubelik, A. R., Livak, K. J., Rafalski, J. A. & Tingey, S. C. (1990) DNA polymorphisms amplified by arbitrary primers are useful as genetic markers. *Nucleic Acids Res.* 18:6531–6535.

Youvan, D. C., Coleman, J. C., Silva, C. M., Petersen, J., Bylina, E. J., & Yang, M. M. 1997. Fluorescence Imaging Micro-Spectrophotometer (FIMS). *Biotechnology et alia*, <www.et-al.com>1:1–16.

What is claimed is:

1. A method for empirically calibrating an optical system, the method comprising the steps of:
   (a) collecting data for calibration in a matrix [G], columns 1 through n of the matrix representing spectral channels, and rows 1 through m of the matrix representing spectral groups;
   (b) solving for a correction matrix [C];
   (c) collecting vector data [Y] for pixels in an image representing the uncorrected intensity of the pixels in each of the 1 through n spectral channels of matrix [G];
   (d) correcting [Y] by matrix multiplication with [C] to obtain empirically calibrated vectors [X] for the pixels in the calibrated image; and
   (e) further correcting the vectors [X] to yield vectors [N] by normalizing the vectors [X] to signals in a specific spectral channel.

2. The method of claim 1, where m equals n in matrix [G], and the correction matrix [C] is the inverse of [G].

3. The method of claim 1, where m is not equal to n in matrix [G], and the correction matrix [C] is solved for by singular value decomposition.

4. The method of claim 1, wherein the optical system is a microscope.

5. The method of claim 4, wherein the microscope operates in an epifluorescent configuration.

6. The method of claim 1, wherein the spectral channels are determined by filter configurations within an epifluorescence microscope.

7. The method of claim 1, wherein the spectral groups correspond to a set of fluorophores used to identify a set of probes.

8. The method of claim 1, where the calibration data is obtained from a calibration sample.

9. The method of claim 1, wherein the image is of a sample comprising cells.

10. The method of claim 9, wherein the cells are members of the same taxa.

11. The method of claim 9, wherein a plurality of probes is bound to the cells.

12. The method of claim 11, wherein the probes comprise oligonucleotides.

13. The method of claim 12, wherein the oligonucleotides are deoxyoligonucleotides.

14. The method of claim 12, wherein the probes hybridize to rRNA.

15. The method of claim 14, wherein the probes hybridize to 16S rRNA.

16. The method of claim 14, wherein the probes hybridize to 16s rRNA.

17. The method of claim 14, wherein the probes hybridize to 23S rRNA.

18. The method of claim 14, wherein the probes hybridize to 28S rRNA.

19. The method of claim 11, wherein the probes are labeled with fluorescent molecules.

20. The method of claim 11, wherein the probes comprise antibodies.

* * * * *

UNITED STATES PATENT AND TRADEMARK OFFICE
CERTIFICATE OF CORRECTION

PATENT NO. : 6,738,502 B1
DATED : May 18, 2004
INVENTOR(S) : William Coleman et al.

It is certified that error appears in the above-identified patent and that said Letters Patent is hereby corrected as shown below:

<u>Column 40,</u>
Line 39, replace "16s" with -- 18s --

Signed and Sealed this

Twenty-fourth Day of August, 2004

JON W. DUDAS
*Director of the United States Patent and Trademark Office*